(12) United States Patent
Johnson et al.

(10) Patent No.: US 11,303,027 B2
(45) Date of Patent: Apr. 12, 2022

(54) METHOD AND APPARATUS TO MOUNT A MEDICAL IMAGING ANTENNA TO A FLEXIBLE SUBSTRATE

(71) Applicant: Neocoil, Inc., Pewaukee, WI (US)

(72) Inventors: Kyle Johnson, Brookfield, WI (US); Michael Haase, New Berlin, WI (US)

(73) Assignee: Neocoil, LLC, Pewaukee, WI (US)

( * ) Notice: Subject to any disclaimer, the term of this patent is extended or adjusted under 35 U.S.C. 154(b) by 260 days.

(21) Appl. No.: 16/247,971

(22) Filed: Jan. 15, 2019

(65) Prior Publication Data

US 2019/0312352 A1 Oct. 10, 2019

Related U.S. Application Data

(60) Provisional application No. 62/653,923, filed on Apr. 6, 2018.

(51) Int. Cl.
*H01Q 7/00* (2006.01)
*H01Q 1/24* (2006.01)
*H01Q 21/00* (2006.01)

(52) U.S. Cl.
CPC .............. *H01Q 7/00* (2013.01); *H01Q 1/24* (2013.01); *H01Q 21/0087* (2013.01)

(58) Field of Classification Search
CPC combination set(s) only.
See application file for complete search history.

(56) References Cited

U.S. PATENT DOCUMENTS

| | | | |
|---|---|---|---|
| 10,263,320 B2* | 4/2019 | Kourti | H01Q 1/273 |
| 10,992,037 B2* | 4/2021 | Rogers | H01Q 1/48 |
| 2009/0009414 A1* | 1/2009 | Reykowski | H01Q 7/04 343/742 |
| 2009/0027053 A1* | 1/2009 | Decke | A61B 5/055 324/318 |
| 2010/0298895 A1* | 11/2010 | Ghaffari | A61N 5/062 607/3 |
| 2011/0034912 A1* | 2/2011 | de Graff | A61B 5/01 606/21 |
| 2013/0321212 A1* | 12/2013 | O'Shea | H01Q 5/371 343/700 MS |
| 2019/0280363 A1* | 9/2019 | Dahle | H01Q 21/065 |
| 2019/0312352 A1* | 10/2019 | Johnson | H01Q 21/0087 |

FOREIGN PATENT DOCUMENTS

WO WO-2010135469 A1 * 11/2010 ............ A61B 5/415

* cited by examiner

*Primary Examiner* — Graham P Smith
*Assistant Examiner* — Jae K Kim
(74) *Attorney, Agent, or Firm* — Boyle Fredrickson, SC

(57) ABSTRACT

A flexible coil includes a flexible substrate with a plurality of holes extending through the substrate. Each hole is configured to receive at least a portion of a fastener extending through the hole. Each fastener engages the flexible substrate and an antenna loop to positively retain the antenna loop to the flexible substrate. The holes are arranged in the flexible substrate to align each antenna loop with respect to the other antenna loops mounted to the flexible substrate. The fasteners are removably mounted to the flexible substrate such that the fastener positively retains the antenna loop to the flexible substrate when mounted to the flexible substrate but allows individual antenna loops to be removed from the flexible substrate when the fastener is removed from the flexible substrate. Multiple fasteners are provided for each antenna loop and are spaced apart from each other and positioned along the length of the loop.

15 Claims, 22 Drawing Sheets

METHOD AND APPARATUS TO MOUNT A MEDICAL IMAGING ANTENNA TO A FLEXIBLE SUBSTRATE

CROSS-REFERENCE TO RELATED APPLICATIONS

This application claims priority to U.S. Provisional Application Ser. No. 62/653,923, filed Apr. 6, 2018, the entire contents of which is incorporated herein by reference.

BACKGROUND OF THE INVENTION

The subject matter disclosed herein relates to a flexible antenna array for medical imaging and, more specifically, to a system for mounting multiple antennas to a flexible substrate to form the flexible antenna array.

As is known to those skilled in the art, a magnetic resonance imaging (MRI) system alternately generates a strong magnetic field which aligns nuclei in the presence of the magnetic field and then detects the faint nuclear magnetic resonance (NMR) signals given off by nuclei returning to a normal state in the absence of the magnetic field. The NMR signals vary as a function of the type of organ, bone, tissue, etc. . . . present within the magnetic field. The NMR signals are received by antennas, also referred to as local coils, and transmitted to the MR scanner for reconstruction into an MR image. Specifically, an anatomical region of a patient is located within the magnetic field and proximate to the antennas. The MR scanner reconstructs the NMR signals into an MR image corresponding to the anatomical region of the patient being imaged.

An antenna loop is configured to detect and send the NMR signals to the host MRI scanner such that trained practitioners make appropriate diagnoses of an anatomical region of interest. Often multiple antenna loops are arranged together, forming an antenna array, to obtain NMR signals from a larger anatomical region. Each antenna loop in the antenna array typically includes a signal conditioning circuit. The signal conditioning circuit is an electronic circuit which receives the NMR signals from the corresponding antenna loop and transmits the NMR signals to the MRI scanner. The signal conditioning circuit may amplify the magnitude of the NMR signals to a suitable level for transmission, perform filtering of the NMR signal to remove unwanted signal components, or perform additional processing of the NMR signal prior to transmitting the NMR signal to the MRI scanner. Each antenna loop and signal conditioning circuit are commonly referred to as a channel for the MRI scanner.

When multiple antenna loops are arranged in an antenna array, it is often desirable to overlap the antenna loops to detect NMR signals from the entire region to be imaged. However, when antenna loops overlap, cross-coupling occurs between overlapping antenna loops, such that a signal detected by one loop may generate an artifact on another loop. Techniques have been developed to arrange the loops and to process the signals with the signal conditioning circuit to minimize or eliminate the artifacts due to the cross-coupling. These techniques typically rely on consistent positioning of the antenna loops with respect to each other. Once the antenna loops have been positioned, the antenna loops must maintain the relationship with respect to the other loops during use and, in particular, with respect to an overlapping relationship between loops.

To facilitate imaging with multiple antenna loops in an antenna array, the antenna arrays have commonly been mounted within a rigid housing. The rigid housing allows the antenna arrays to be precisely positioned within the housing, and during use the rigid housing protects the antenna arrays and retains the consistent positioning of the antenna loops in their original relationship with each other. The housings may take on different shapes corresponding to the shape of the anatomical region of interest. The shape of a housing to fit, for example, over a shoulder is necessarily different than the shape of a housing used to image a foot. Similarly, the antenna arrays and housings need to adapt for variations in the size of a particular anatomical region. The same housing sized to fit a pediatric torso will not fit the torso of a large adult. As a result, the antenna arrays and their corresponding housings (also referred to as a coil) must be designed to accommodate a broad range of anatomical regions of varying sizes, and imaging centers are required to invest in a significant number of coils to cover all imaging applications.

In order to reduce the number of coils an imaging center requires, developments have been made in manufacturing flexible antenna coils. However, the flexible antenna coil must similarly be able to maintain the consistent positioning of individual antenna loops with respect to each other in order to avoid introducing unwanted artifacts in an image. Typically, a flexible antenna coil includes multiple antenna loops made from a flexible material mounted to a flexible, thin film substrate, such as KAPTON®. The antenna loops are securely mounted, for example, with an adhesive material or other bonding technique to maintain the desired positioning of each antenna loop with respect to the other on the flexible substrate. The signal conditioning circuits for each antenna loop are similarly mounted to or positioned on the flexible substrate. The antenna loops and flexible substrate are then covered in an interior layer of foam surrounding the antenna and their associated electronic components and an exterior layer made, for example, of a plastic, nylon, rubber, or combination thereof. The foam is included for patient comfort and the external layer is included as a protective layer for the foam and the antennas on the interior to withstand regular contact with the patient, the imaging table, and the like.

Serviceability of a coil is another important consideration for selecting an imaging system. If one of the antenna loops or other electronic components in a flexible coil were to fail, typically, the entire flexible substrate must be removed and replaced, including all of the antenna loops. This is due, in part, to the manner in which the antenna loops are secured to the flexible substrate and, in part, to the nature of the flexible substrate. This often results in damage to the flexible substrate if replacing one of the antenna loops is attempted.

Thus, it would be desirable to provide a system for mounting antennas to the flexible substrate that facilitates repair and/or replacement of the antennas or other electronic components in a flexible coil, reducing repair time and reducing lost time and revenue of the imaging center.

BRIEF DESCRIPTION OF THE INVENTION

The subject matter disclosed herein describes a system for mounting antennas to a flexible substrate that facilitates repair and/or replacement of the antennas or other electronic components in a flexible coil. A flexible substrate is provided with a plurality of holes extending through the substrate. Each hole is configured to receive at least a portion of a fastener extending through the hole. Optionally, the flexible substrate may include a pierce point, or small hole, which is smaller than the width of the fastener to be inserted but provides a starting point for insertion of the fastener. As the fastener is inserted through the flexible substrate the opening expands around the fastener. In still another embodiment, the flexible substrate may include markers, or indicia, located on the flexible substrate to identify a location at which a fastener is to be inserted. The fastener may include pins or other sharp points configured to pierce the flexible substrate at the locations identified by the markers. For convenience, the invention will be described herein with respect to holes located in the flexible substrate. However, it is understood that the holes may be replaced by the pierce points or markings according to the desired fastener to be used to secure the antenna loops to the flexible substrate.

Each fastener engages the flexible substrate and an antenna loop to positively retain the antenna loop to the flexible substrate. The holes are arranged in the flexible substrate to align each antenna loop with respect to the other antenna loops mounted to the flexible substrate. The fasteners are removably mounted to the flexible substrate such that the fastener positively retains the antenna loop to the flexible substrate when mounted to the flexible substrate but allows individual antenna loops to be removed from the flexible substrate when removed from the flexible substrate. A plurality of fasteners are provided for each antenna loop and are spaced apart from each other and positioned along the length of the loop.

According to one embodiment of the invention, a system for assembling a flexible antenna array for medical imaging is disclosed. The system includes a flexible substrate, multiple antennas, and multiple fasteners. The flexible substrate has a plurality of holes extending therethrough, and the antennas are operative to receive a signal corresponding to an anatomical region of a patient during medical imaging. Each fastener is removably mounted to the flexible substrate through at least one of the holes in the flexible substrate and is operative to secure one of the antennas to the flexible substrate.

According to another aspect of the invention, each fastener extends through a first hole and a second hole in the flexible substrate, and each antenna is positioned between the first hole and the second hole for one of the fasteners when secured to the flexible substrate.

According to still another aspect of the invention, each of the plurality of fasteners may include a first member and a second member. The first member has a first segment, configured to extend through the first hole in the flexible substrate, and a second segment, pivotally mounted to the first segment. The second member is configured to extend through the second hole in the flexible substrate, and the second segment of the first member pivots towards and positively engages the second member to retain one of the plurality of antennas to the flexible substrate. The first member may include a living hinge between the first segment and the second segment.

According to yet another aspect of the invention, each fastener may include a first half fastener and a second half fastener. The first half fastener includes a first boss proximate a first end of the first half fastener and a first opening proximate a second end of the first half fastener, where the first boss is configured to extend through the first hole in the flexible substrate from a first side of the flexible substrate. The second half fastener includes a second boss proximate a first end of the second half fastener and a second opening proximate a second end of the second half fastener, where the second boss extends through the second hole in the flexible substrate from a second side of the flexible substrate. The first boss engages the second opening and the second boss engages the first opening to positively retain one of the plurality of antennas to the planar flexible substrate.

According to another aspect of the invention, the fastener may include a first side portion, a second side portion, and a middle segment extending between the first and second side portions to positively retain one of the plurality of antennas to the planar flexible substrate. Each of the first and second side portions includes an upper segment configured to be located on a first side of the flexible substrate when the fastener is mounted to the flexible substrate, a lower segment configured to be located on a second side of the flexible substrate when the fastener is mounted to the flexible substrate, and a rear segment configured to extend through one of the plurality of holes in the flexible substrate between the upper and lower segment. The upper segment, the lower segment, and the rear segment define a channel configured to receive the flexible substrate. The lower segment may include at least one resilient member, where the resilient member has a first width greater than a width of each of the plurality of holes when the resilient member is in a first position and a second width less than the width of each of the plurality of holes when the resilient member is in a second position.

According to still another aspect of the invention, the system may include a web connected to each of the fasteners operative to secure a first antenna to the flexible substrate. The web is operative to position each of the fasteners proximate to the first hole and the second hole in the flexible substrate through which the fastener extends. In one embodiment, the web may include multiple segments, each segment having a first end and a second end. The first end of each segment is connected to a first fastener and the second end of each segment is connected to a second fastener. In another embodiment, the web may include multiple segments, each segment having a first end and a second end. The first end of each of the segments is connected together at a central point, and the second end of each of the segments is connected to one of the fasteners. In still another embodiment, the web may include multiple first segments and multiple second segments. Each of the first segments includes a first end and a second end, where the first end of each first segment is connected to the second end of another first segment. Each of the second segments includes a first end and a second end, where the first end of each of the second segments is connected to one of the first segments, and the second end of each of the second segments is connected to one of the plurality of fasteners.

According to another embodiment of the invention, a method for assembling a flexible antenna array for medical imaging is disclosed. Multiple holes are created through a flexible substrate, and multiple antennas are positioned on the flexible substrate. Each antenna is operative to receive a signal corresponding to an anatomical region of a patient during medical imaging. Multiple fasteners are inserted through the holes in the flexible substrate, and each fastener is removably mounted to the flexible substrate. Each fastener extends through at least one of the holes in the flexible substrate, and each fastener is operative to secure one of the antennas to the flexible substrate.

According to another aspect of the invention, each of the plurality of fasteners may include at least one piercing member to cut a hole through the flexible substrate and the step of creating the holes is done by the at least one piercing member as each fastener is inserted through the flexible substrate.

According to yet another embodiment of the invention, a system for assembling a flexible antenna array for medical imaging includes a flexible substrate, multiple antennas, and multiple fasteners. The flexible substrate has multiple holes extending therethrough, and the antennas are operative to receive a signal corresponding to an anatomical region of a patient during medical imaging. Each fastener includes a base, a first member, and a second member. The first member extends from the base and has a first segment and a second segment pivotally mounted to the first segment. The second member extends from the base in the same direction as the first member, and each of the first and second members are configured to extend through one of the holes in the flexible substrate. The second segment of the first member pivots towards and is removably connected to the second member to retain one of the antennas to the flexible substrate. The first member may also include a living hinge between the first segment and the second segment, where the second segment is pivotally mounted to the first segment via the living hinge.

These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWING(S)

Various exemplary embodiments of the subject matter disclosed herein are illustrated in the accompanying drawings in which like reference numerals represent like parts throughout, and in which.

Figure 1:
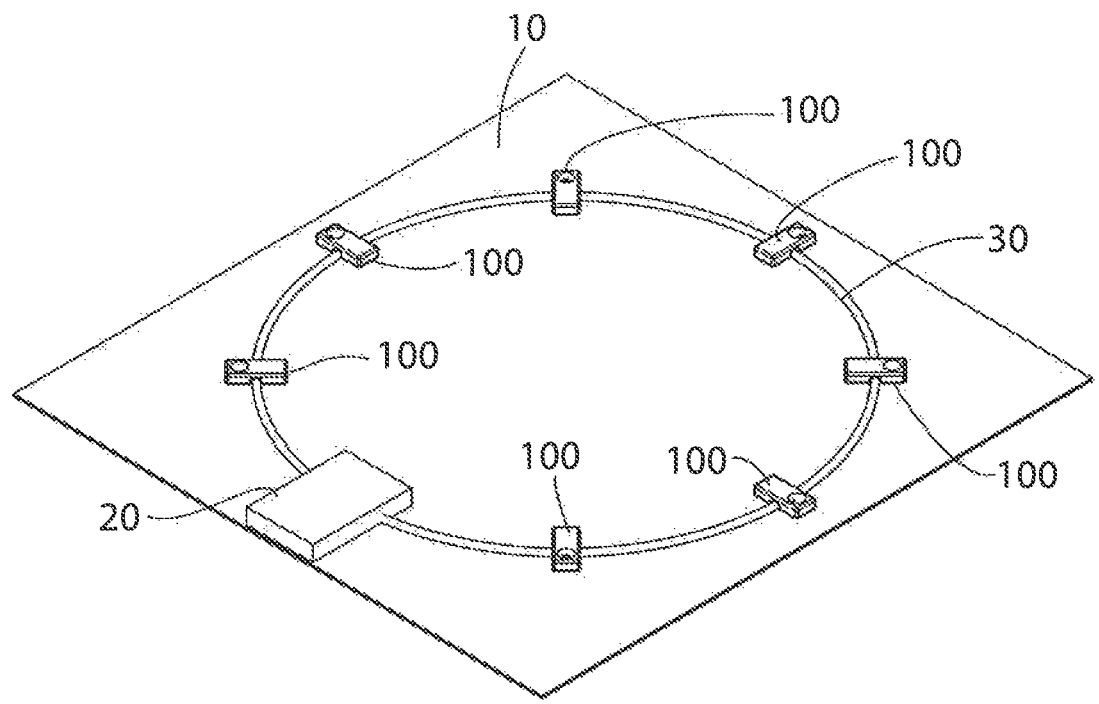
FIG. 1 is an isometric view of a single antenna loop mounted to a flexible substrate according to one embodiment of the present invention.

In describing the preferred embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements where such connection is recognized as being equivalent by those skilled in the art.

DETAILED DESCRIPTION OF THE PREFERRED EMBODIMENTS

The various features and advantageous details of the subject matter disclosed herein are explained more fully with reference to the non-limiting embodiments described in detail in the following description.

Figure 2:
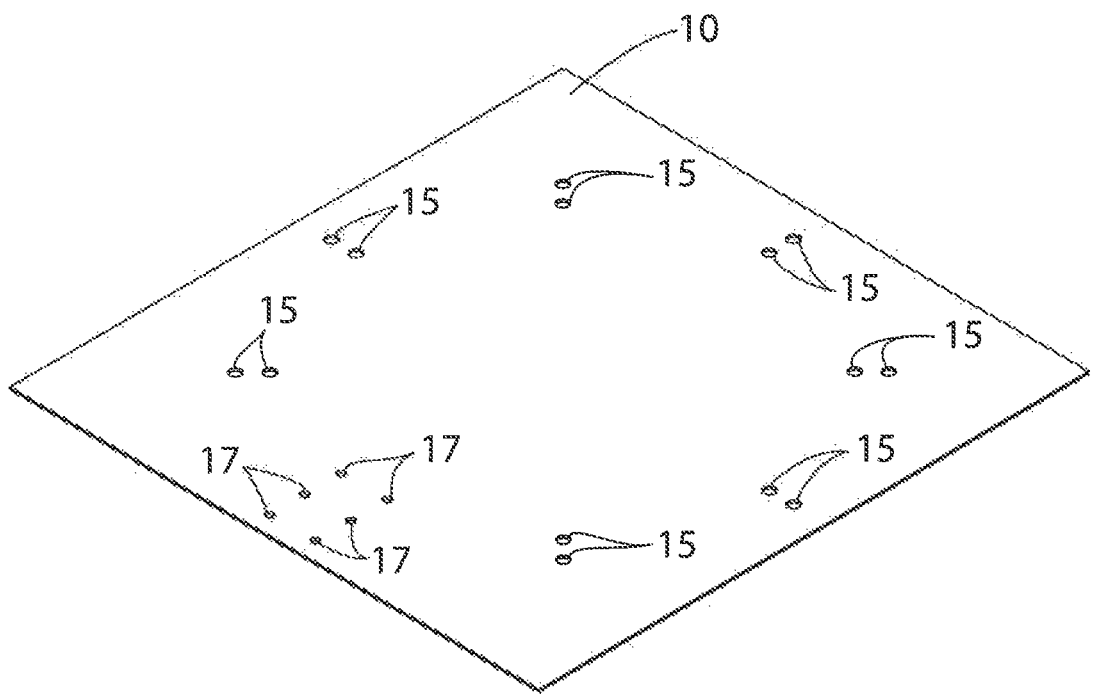
FIG. 2 is an isometric view of the flexible substrate of FIG. 1.
Figure 3:
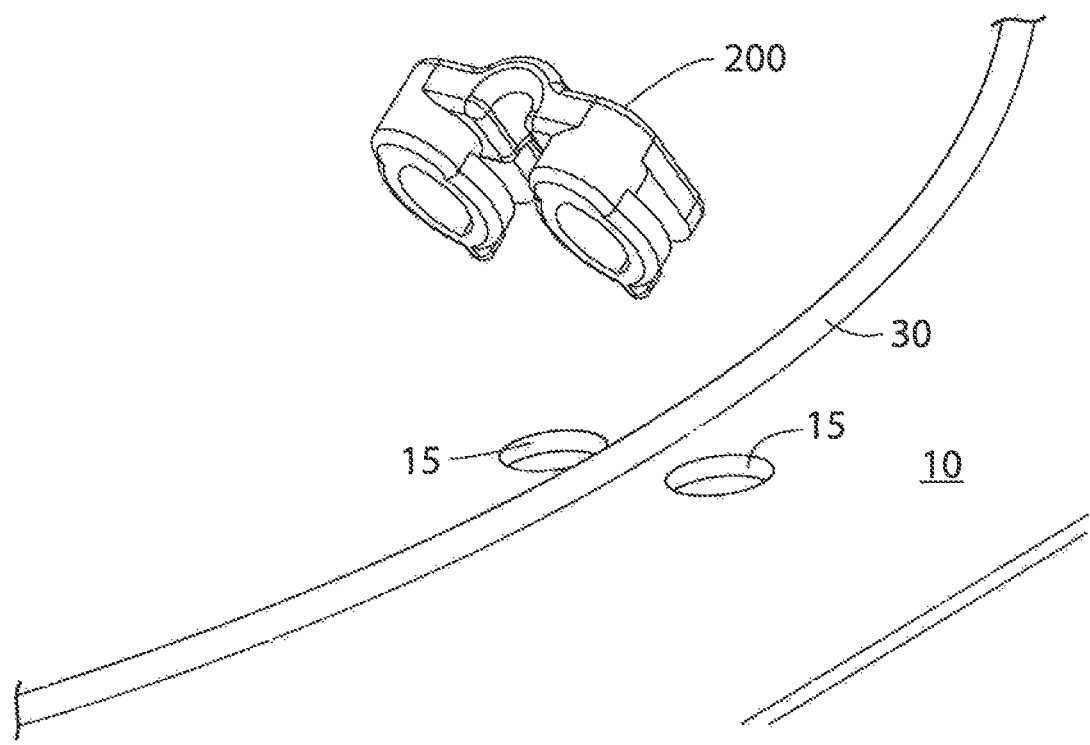
FIG. 3 is a partial isometric vies of the antennal loop, a fastener, and the flexible substrate according to another embodiment of the present invention.
Figure 4:
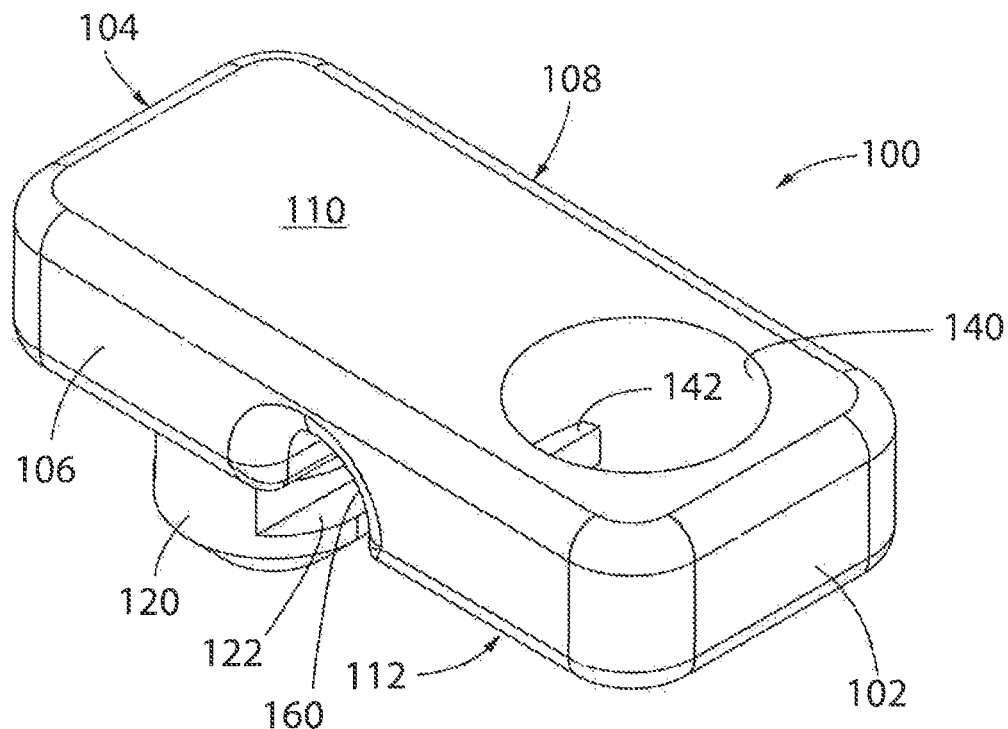
FIG. 4 is an isometric view of one half of a fastener to secure the antenna loop to the flexible substrate according to the embodiment shown in FIG. 1.
Figure 5:
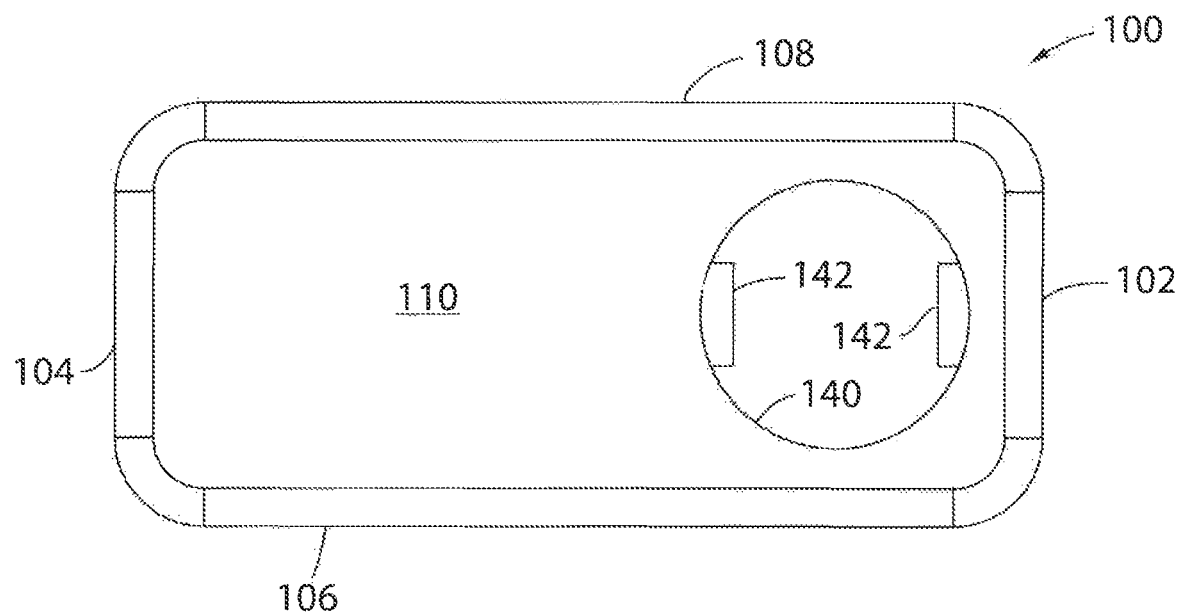
FIG. 5 is a top plan view of the fastener of FIG. 4.
Figure 6:
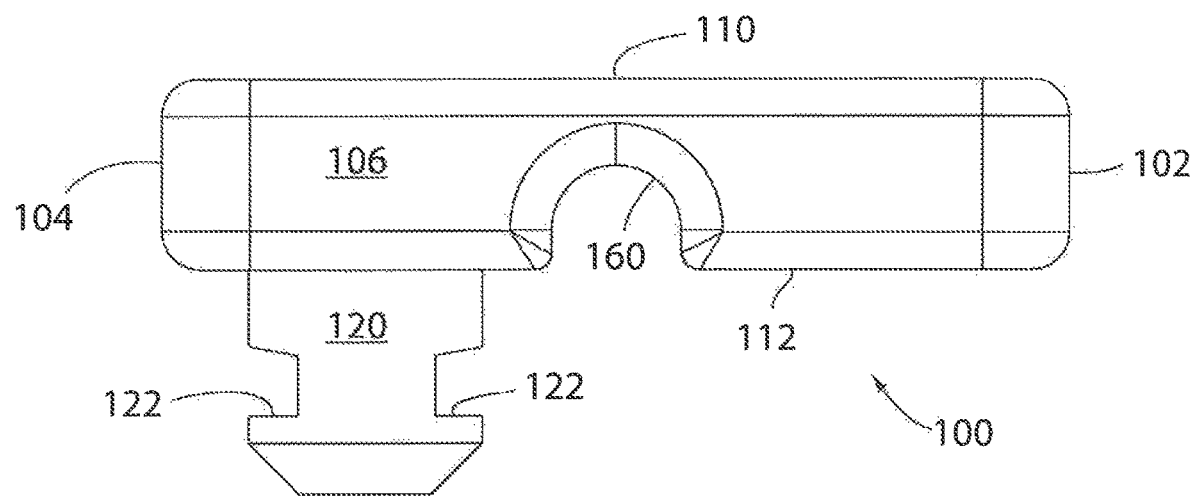
FIG. 6 is a side elevation view of the fastener of FIG. 4.
Figure 7:
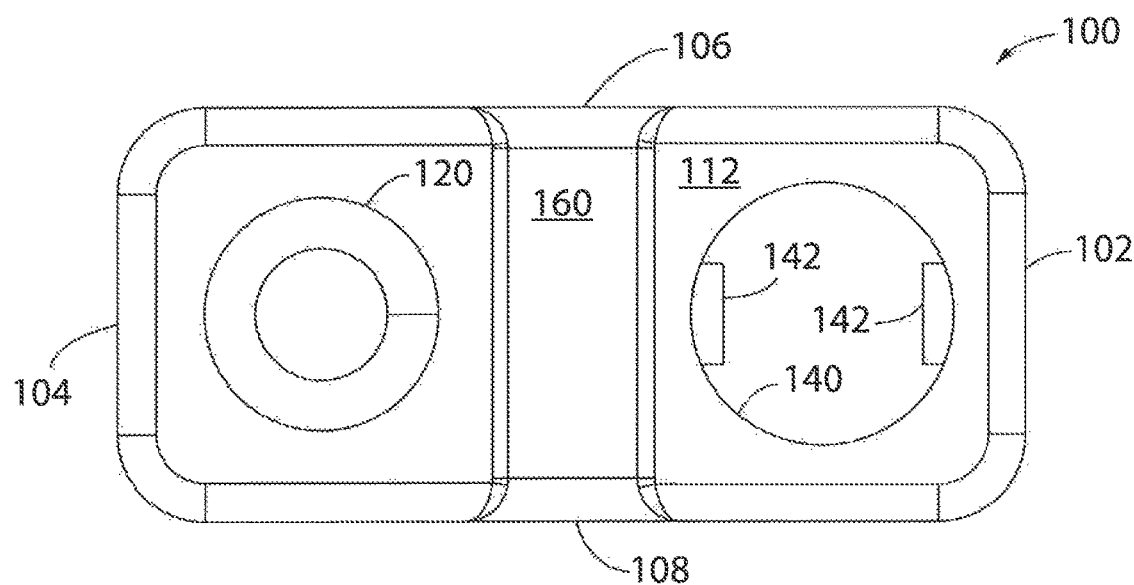
FIG. 7 is a bottom plan view of the fastener of FIG. 4.
Figure 8:
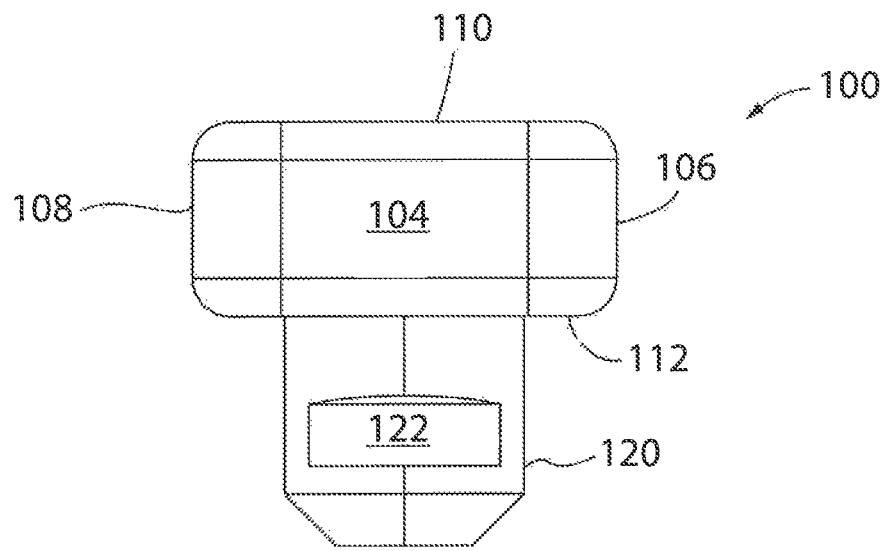
FIG. 8 is an elevation view of a first end of the fastener of FIG. 4.
Figure 9:
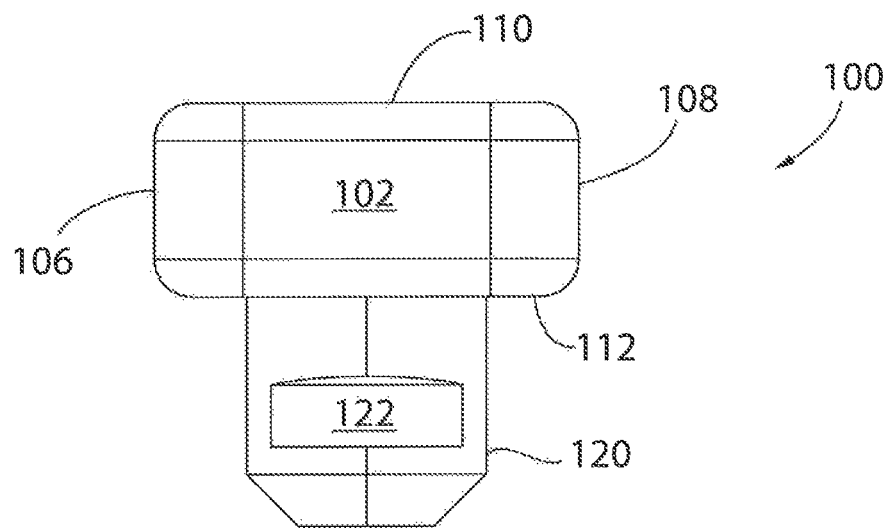
FIG. 9 is an elevation view of a second end of the fastener of FIG. 4.
Figure 10:
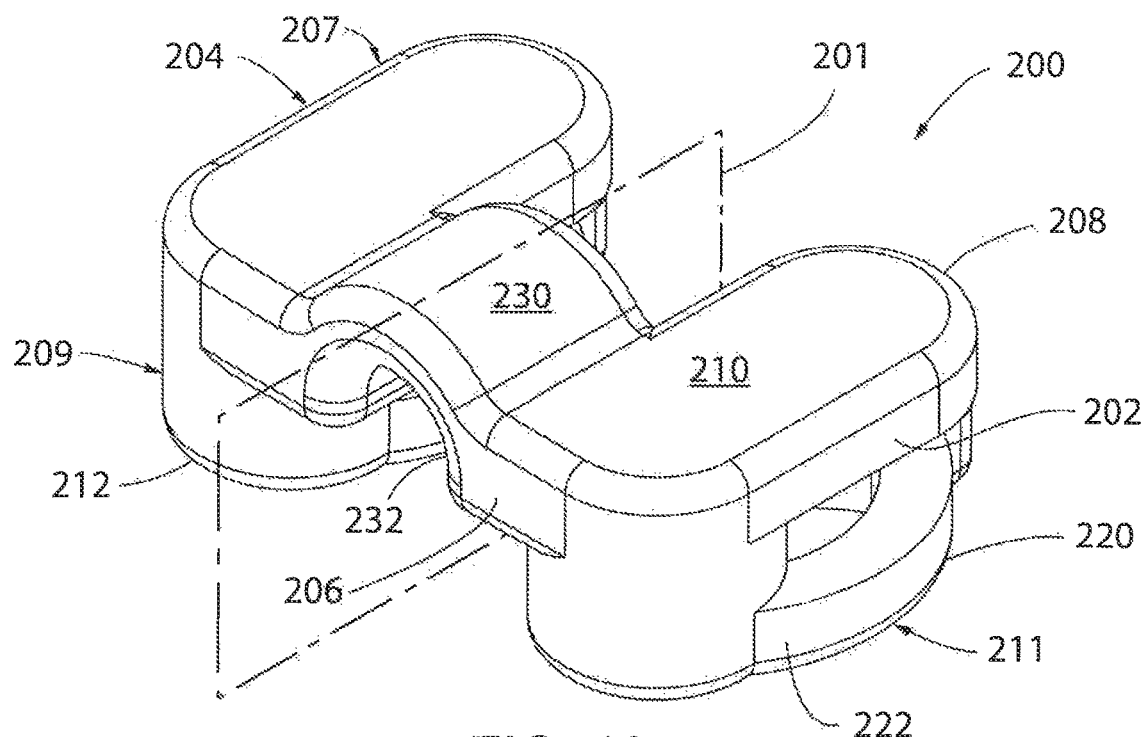
FIG. 10 is an isometric view of a fastener to secure the antenna loop to the flexible substrate according to the embodiment shown in FIG. 3.
Figure 11:
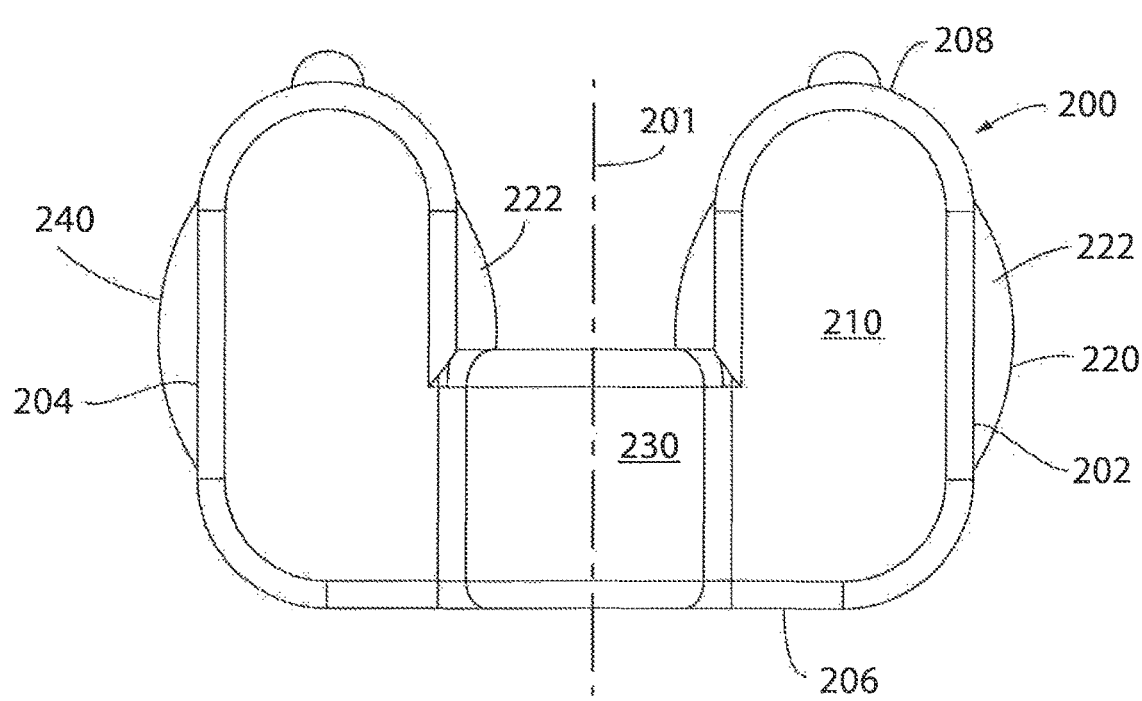
FIG. 11 is a top plan view of the fastener of FIG. 10.
Figure 12:
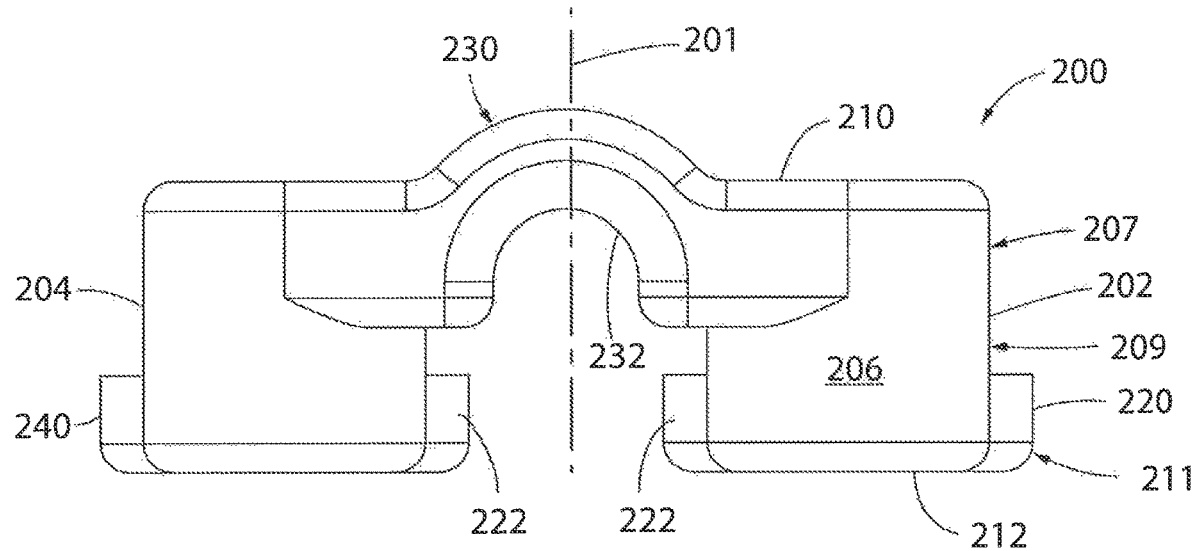
FIG. 12 is a rear elevation view of the fastener of FIG. 10.
Figure 13:
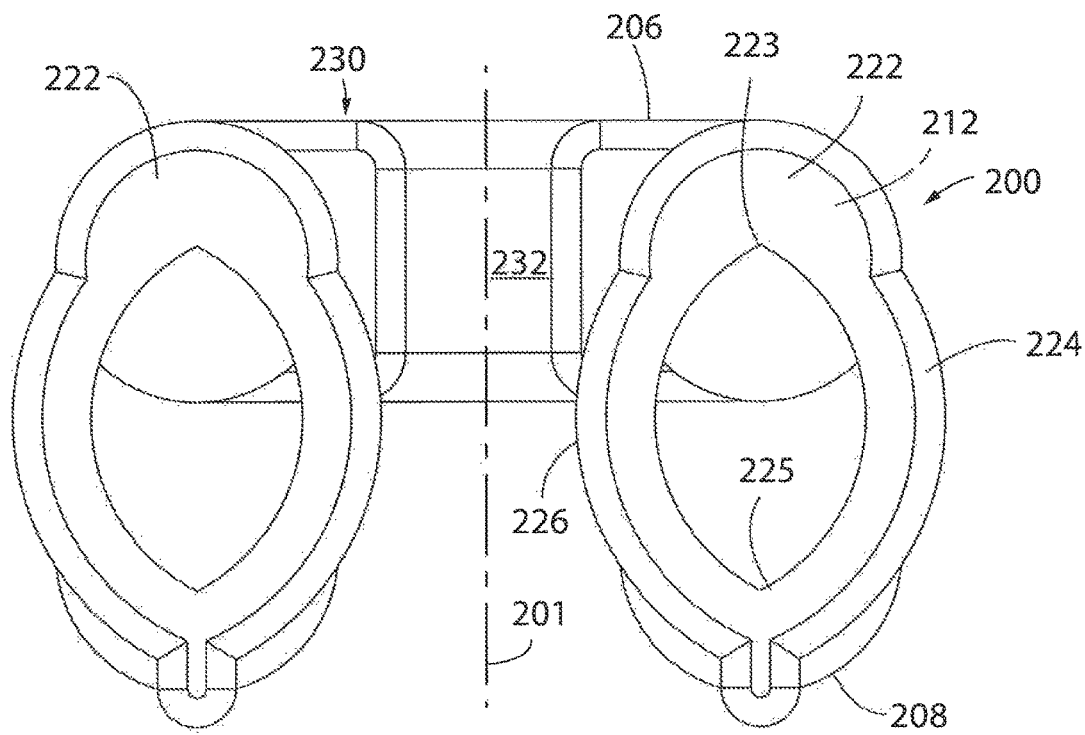
FIG. 13 is a bottom plan view of the fastener of FIG. 10.
Figure 14:
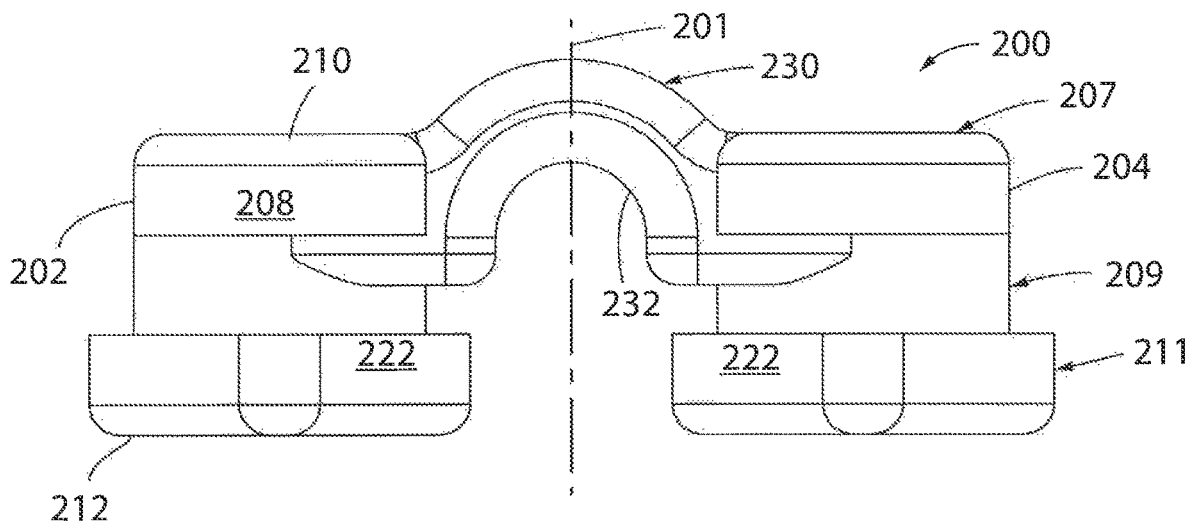
FIG. 14 is a front elevation view of the fastener of FIG. 10.
Figure 15:
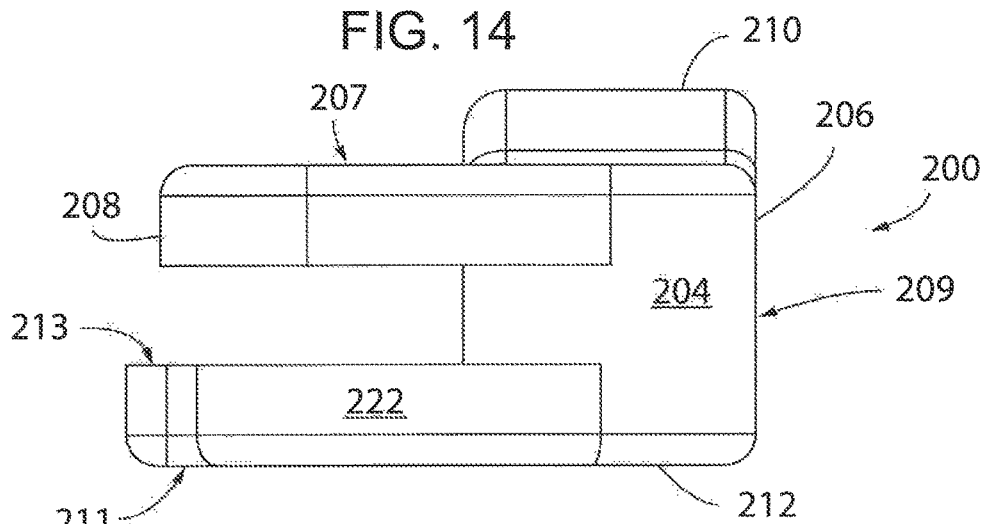
FIG. 15 is a right elevation view of the fastener of FIG. 10.
Figure 16:
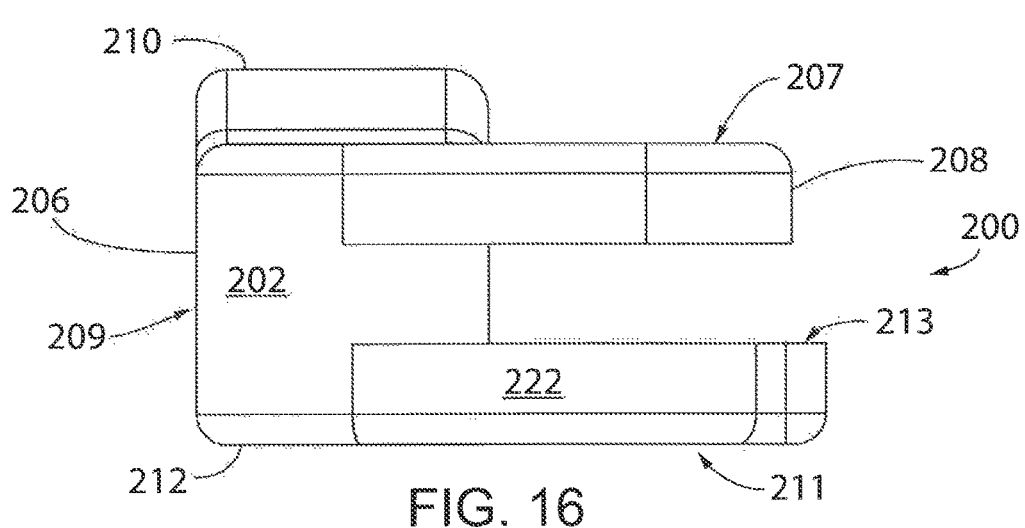
FIG. 16 is a left elevation view of the fastener of FIG. 10.
Figure 17:
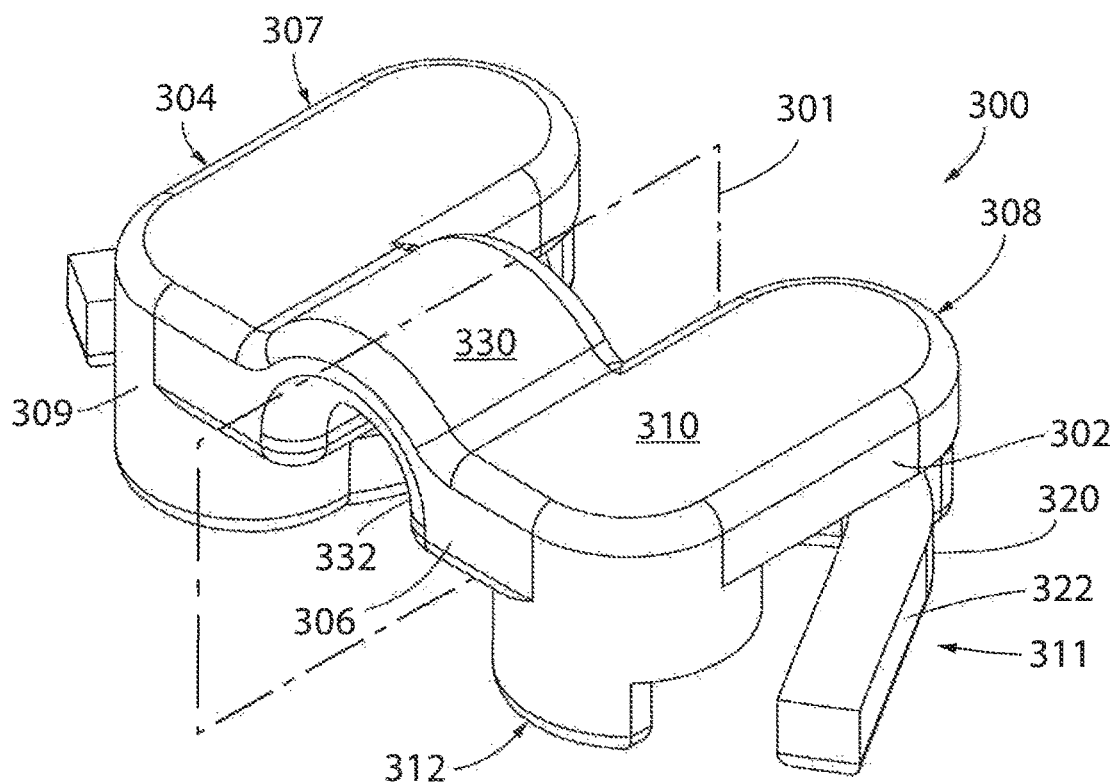
FIG. 17 is an isometric view of a fastener to secure the antenna loop to the flexible substrate according to another embodiment of the present invention.
Figure 18:
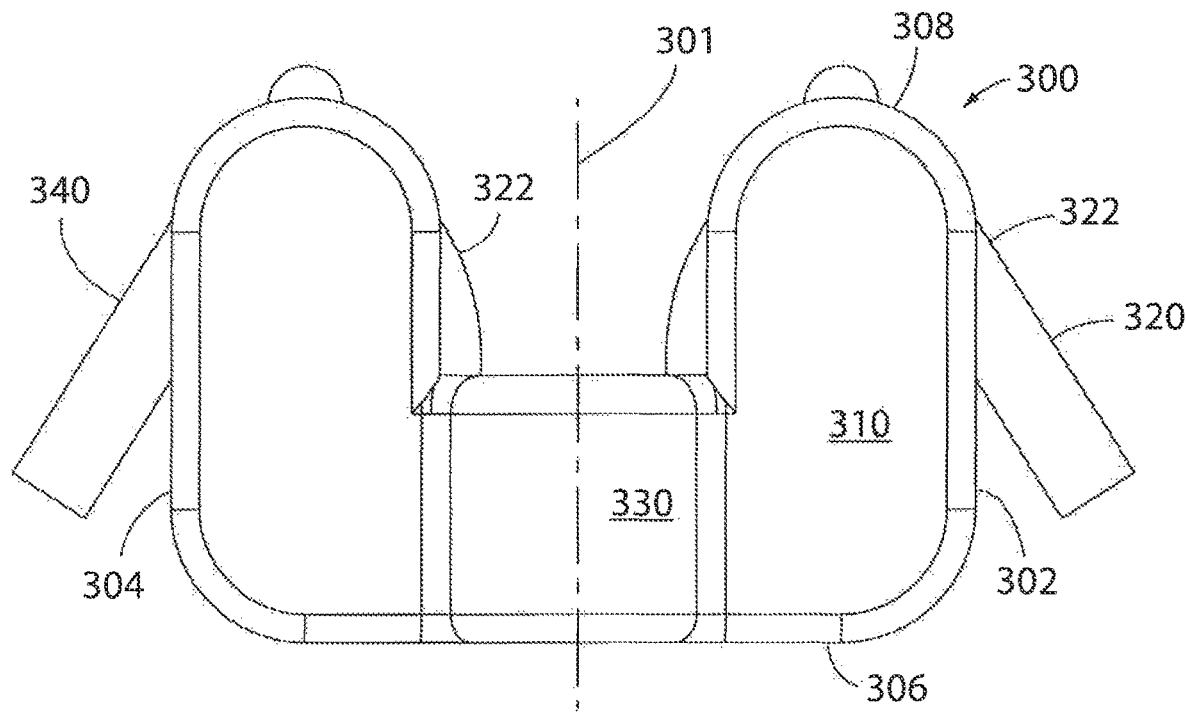
FIG. 18 is a top plan view of the fastener of FIG. 17.
Figure 19:
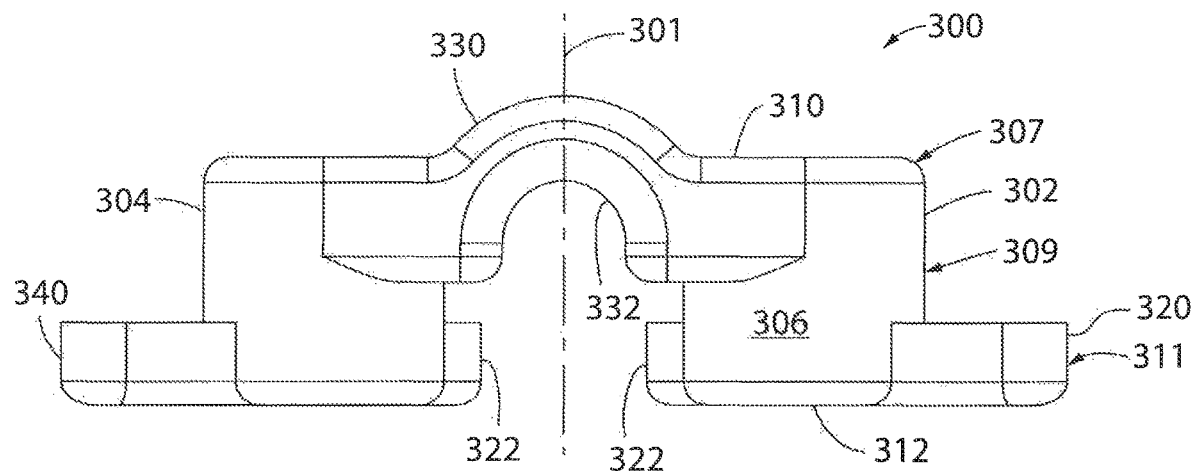
FIG. 19 is a rear elevation view of the fastener of FIG. 17.
Figure 20:
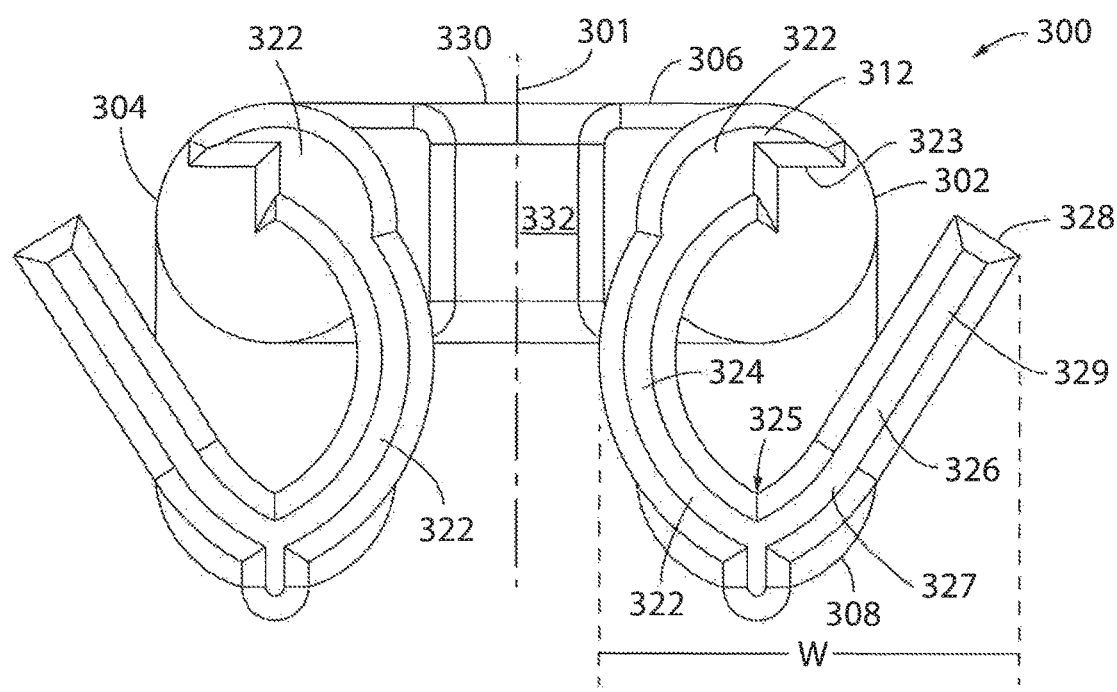
FIG. 20 is a bottom plan view of the fastener of FIG. 17.
Figure 21:
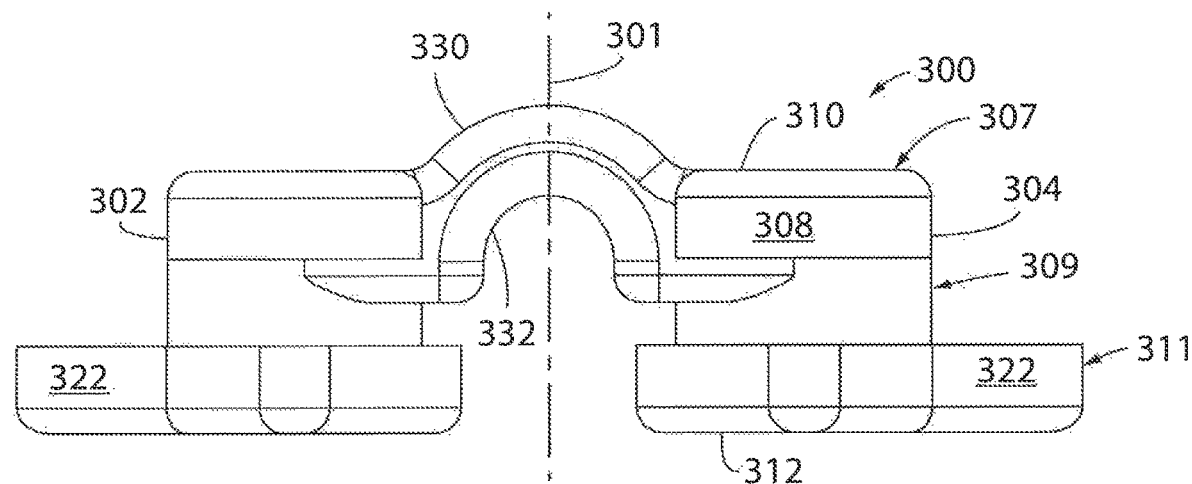
FIG. 21 is a front elevation view of the fastener of FIG. 17.
Figure 22:
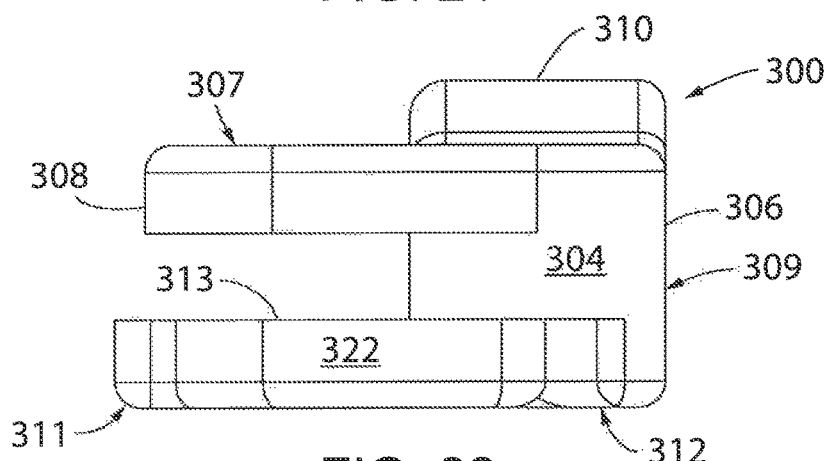
FIG. 22 is a right elevation view of the fastener of FIG. 17.
Figure 23:
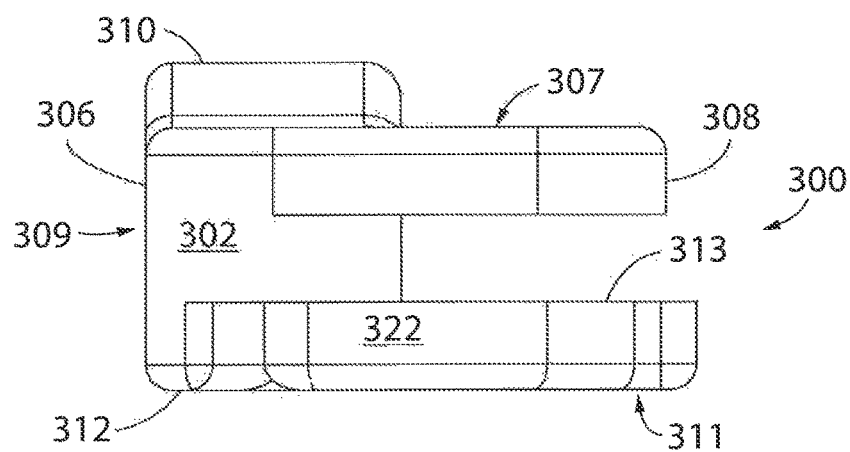
FIG. 23 is a left elevation view of the fastener of FIG. 17.
Figure 24:
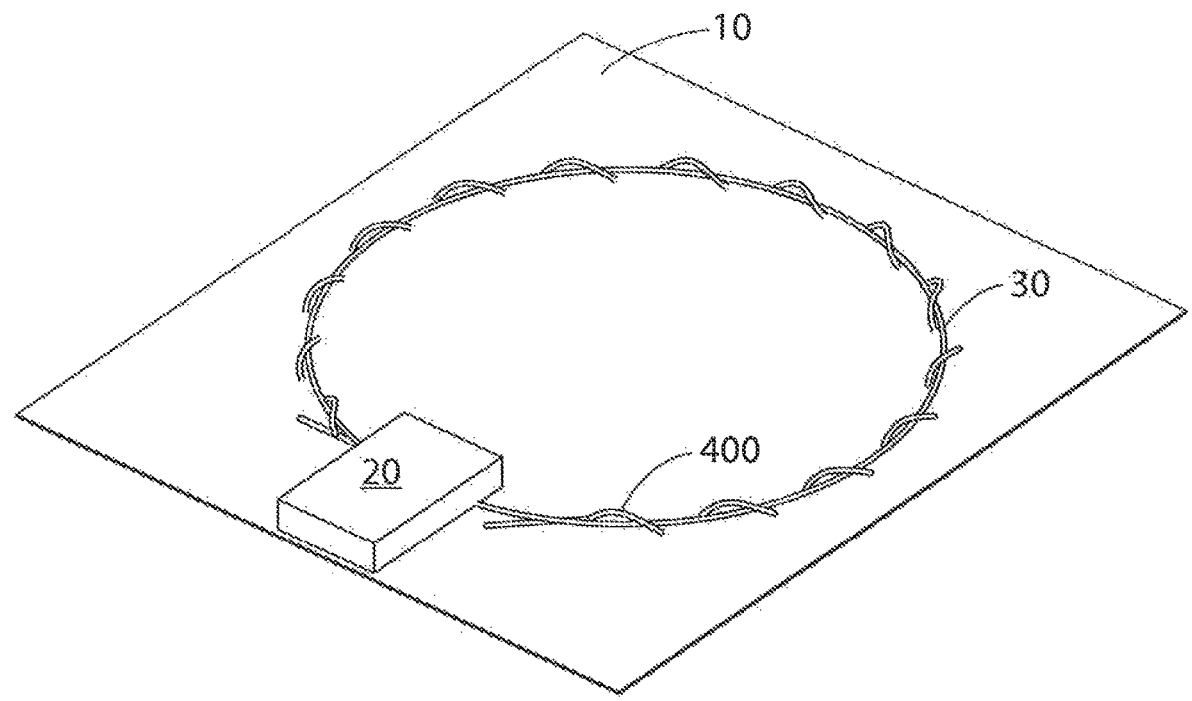
FIG. 24 is an isometric view of a single antenna loop mounted to a flexible substrate according to another embodiment of the present invention.

Turning initially to FIGS. 1 and 2, a system for assembling a flexible antenna array according to one embodiment of the invention is illustrated. According to the illustrated embodiment, a flexible substrate 10 is provided to which an antenna loop 30 is mounted. The flexible substrate 10 is made of a material that is invisible to the medical imaging system. In a magnetic resonance imaging (MRI) scanner, therefore, the flexible substrate is made of a material that is not excited by the presence of the magnetic field generated by the MRI scanner. As a result, the flexible substrate 10 does not generate an image artifact and is not observable when an object is being imaged by the MRI scanner. Further, the flexible substrate 10 and objects connected to the flexible substrate, such as the fasteners, as will be described in more detail below, are made from a material that is not susceptible to magnetic fields. In other words, the materials are not affected by the magnetic field gradients generated by the MRI scanner.

According to one embodiment of the invention, the flexible substrate 10 is made from a fibrous material. The fibrous material may be a natural or a synthetic fiber. In one embodiment, the flexible substrate 10 is a para-aramid synthetic fiber. Preferably, the synthetic fiber exhibits little elasticity in the plane of the fabric such that its original form factor is retained during use in medical imaging. However, the fibrous material allows the flexible substrate 10 to be positioned on an object to be imaged, for example, by draping the flexible substrate 10 on the object and the flexible substrate 10 conforms to the shape of the object. In other words, the synthetic fiber resists stretching but allows rolling, folding, or other such forces to position the flexible substrate 10. When the antenna array is affixed to the flexible substrate 10, the flexible antenna array is positioned on an object, such as a patient or a portion of the patient's anatomy, to be imaged. The flexible substrate 10 is, therefore, made from a material with an elasticity low enough that the antenna loops 30 affixed to the material maintain a desired relationship with the other antenna loops 30. In particular, it is desirable for the antenna loops 30 to maintain their relative position to adjacent antenna loops on the flexible substrate 10 as a result of the flexible substrate 10 stretching while positioning the flexible antenna array over the object to be imaged.

It is further contemplated that the flexible substrate 10 may be made from a woven material. As also illustrated in FIGS. 1 and 2, a series of holes 15, 17 are made through the flexible substrate 10. The holes 15, 17 may be cut, for example, by drilling, stamping, die cutting, laser cutting, or the like in the flexible substrate 10. A first series of holes 15 are provided to receive a fastener 100, 200, 300, 400, or 500 or a portion of a fastener extending through the hole 15. A second series of holes 17 are provided for securing a circuit board or housing 20 containing a circuit board on which an electronic circuit for the antenna loop 30 is mounted. The illustrated embodiment shows the housing 20 as a rectangular box. It is contemplated that various other shapes for the housing 20 may be utilized. Optionally, the circuit board may also be mounted directly to the flexible substrate 10.

Turning next to FIGS. 4-9, an exemplary embodiment of one half of a fastener 100 to secure an antenna loop 30 to the flexible substrate 10 is illustrated. The fastener 100 includes two halves, where each half is identical. For ease of illustration, only one half is illustrated. A first half of the fastener 100 is inserted through the holes 15 from one side of the flexible substrate 10, and a second half of the fastener 100 is inserted through the holes 15 from the other side of the flexible substrate 10 such that the two halves of the fastener 100 engage each other to positively retain the two halves of the fastener 100 to the flexible substrate 10.

The fastener 100 includes a generally rectangular portion having a first end 102 and a second end 104, where the second end 104 is opposite the first and 102. The generally rectangular portion further includes a first side 106 and a second side 108, where the second side 108 is opposite the first side 106. The generally rectangular portion further includes a top surface 110 and a bottom surface 112, where the bottom surface 112 is opposite the top surface 110. Each of the edges of the generally rectangular portion is curved between adjacent surfaces. The fastener 100 further includes a boss 120, protruding from the bottom surface 112 proximate the second end 104 of the generally rectangular portion, and an opening 140, extending through the generally rectangular portion proximate the first end 102. The boss 120 of a first half of the fastener 100 is configured to engage the opening 140 of a second half of the fastener 100. Similarly, the boss 120 of a second half of the fastener 100 is configured to engage the opening 140 of the first half of the fastener 100. The two halves of the fastener 100 are positioned such that the bottom surface 112 of one half of the fastener faces the bottom surface 112 of the other half of the fastener. The boss 120 of one half of the fastener is aligned with the opening 140 of the other half of the fastener in the two halves of the fasteners are pressed together. The boss 120 on each half of the fastener 100 includes at least one recess 122 configured to receive a tab 142 protruding from an inner periphery of the opening 140. As the two halves of the faster 100 are inserted into each other, the tab 142 in the opening 140 of one half engages the recess 122 on the boss 120 of the other half to retain the two halves together. Optionally, the boss 120 may include a tab protruding from an outer periphery of the boss and the opening 140 may include a recess on the inner periphery of the opening 140 that is configured to receive the tab protruding from the boss 120.

According to the illustrated embodiment, the faster 100 further includes a channel 160 extending along the bottom surface 112 and between the first side 106 and the second side 108 of the fastener. The channel 160 is configured to receive the antenna loop 30. The size of the channel 160 is preferably configured to positively retain the antenna loop 30 in a particular alignment on the flexible substrate 10. Optionally, the periphery of the channel 160 may be larger than the antenna loop 30 to facilitate positioning of the antenna loop 30 after the fastener 100 has been mounted on the flexible substrate 10. The portion of the fastener including the channel 160 may be configured to be deformed, for example, by heat, vibration, pressure, or other known manufacturing methods to securely form the channel around the antenna loop 30. Optionally, an external material, such as a solvent, adhesive, or potting material may be applied to the channel 160 to cause the channel 160 to deform, adhere the antenna loop 30 within the channel, or otherwise positively retain the antenna loop 30 at a desired position within the channel 160.

It is noted that where relational terms such as top and bottom, left and right, upper and lower, and the like are utilized to define aspects of the invention, the terms are not intended to be limiting. The terms are intended to identify relationships between surfaces on a component itself and may be reversed, for example, by turning or rotating a component. It is contemplated that the invention disclosed and defined herein extends to all alternative combinations or orientations of two or more of the individual features of the elements mentioned or evident from the text and/or drawings presented herein.

Turning next to FIGS. 10-16, a second embodiment of a fastener 200 to secure the antenna loop 30 to the flexible substrate 10 is illustrated. The fastener 200 is of single-part, molded construction. The fastener 200 is symmetric about a central plane 201 extending through the fastener 200. The fastener 200 includes a first side 202 and a second side 204, where the second side 204 is opposite the first side 202. The fastener 200 includes a front side 208 and a rear side 206, where the rear side 206 is opposite the front side 208. The fastener also includes a top surface 210 and a bottom surface 212, where the bottom surface 212 is opposite the top surface 210.

The fastener 200 further includes two portions configured to be inserted into the holes 15 in the flexible substrate 10. A first portion 220 is proximate the first side 202 of the fastener 200 and a second portion 240 is proximate a second side 204 of the fastener 200. The first portion 220 is identical to, and symmetrical about the central plane 201 with the second portion 240. When inserted through the holes 15 in the flexible substrate 10, the first portion 220 and the second portion 240 positively retain the fastener 200 to the flexible substrate 10. For convenience, one side of the fastener 200 will be described in detail, where the second side is symmetrical about the plane 201 extending through the fastener 200 and is identical to the first side described below.

When viewed from the side 202, the fastener 200 is generally "c-shaped." The fastener 200 includes an upper segment 207, which is configured to be positioned on one surface of the flexible substrate 10, and a lower segment 211, which is configured to be positioned on the opposite surface of the flexible substrate 10 when the fastener 200 is inserted into the flexible substrate. The upper segment 207 extends generally parallel to the lower segment 211 and is connected by a rear segment 209 extending between the upper and lower segments. A channel 213 is defined between the upper segment 207, rear segment 209, and lower segment 211, where the channel 213 has a width generally equal to or less than the thickness of the flexible substrate 10. The flexible substrate 10, therefore, fits within the channel 213 or is slightly compressed as it is inserted into the channel 213 while the fastener 200 is inserted through the holes 15 of the substrate.

The lower segment 211 includes a resilient member 222 having a width, W, greater than a width of the hole 15 in the flexible substrate 10. According to the embodiment illustrated in FIG. 13, the resilient member 222 is elongated with a first arcuate side member 224 and a second arcuate side member 226 each extending generally from the rear side 206 to the front side 208 of the fastener 200. Each arcuate side member 224, 226 meets at a first point 223 proximate the rear side 206 and a second point 225 proximate the front side 208 with the arcuate side member extending outward and returning inward between the two points. In order to insert the fastener 200 into the holes 15 of the flexible substrate 10, the two arcuate side members 224, 226 are pressed together such that the width, W, of the resilient member 222 is less than the width of the hole 15 in the substrate 10. Pressing the two arcuate side members 224, 226 together causes the resilient member to pivot at each of the first point 223 and the second point 225 and become more elongated. The front end of the resilient member 222 is inserted through the hole 15 and to the bottom side of the flexible substrate 10. When the resilient member 222 has passed through the hole 15, the arcuate side members 224, 226 are released and they return to their original position. Each arcuate side member 224, 226 expands outward under the bottom side of the flexible substrate 10, shortening the length of the resilient member, and the width, W, of the resilient member 222 again becomes greater than the width of the hole 15, preventing the fastener 200 from pulling back through the hole 15. With the flexible substrate 10 located in the channel 213 of the fastener 200 and the resilient member 222 retaining the fastener 200 in the substrate 10, the fastener 200 is securely mounted to the flexible substrate 10.

The fastener 200 further includes a middle segment 230 configured to secure the antenna loop 30 to the flexible substrate 10. The middle segment 230 includes a channel 232 extending from the rear side 206 to the front side 208 of the fastener 200. The channel 232 starts at a height generally equal to the lower surface of the upper segment 207 and extends upward for a height generally equal to an expected thickness of the antenna loop 30. Thus, the channel 232 is configured to receive the antenna loop 30 and to positively retain the antenna loop 30 against the flexible substrate 10 and in a particular alignment on the flexible substrate 10.

Turning next to FIGS. 17-23, a third embodiment of a fastener 300 to secure the antenna loop 30 to the flexible substrate 10 is illustrated. The fastener 300 is of single-part, molded construction. The fastener 300 is symmetric about a central plane 301 extending through the fastener 300. The fastener 300 includes a first side 302 and a second side 304, where the second side 304 is opposite the first side 302. The fastener 300 includes a front side 308 and a rear side 306, where the rear side 306 is opposite the front side 308. The fastener also includes a top surface 310 and a bottom surface 312, where the bottom surface 312 is opposite the top surface 310.

The fastener 300 further includes two portions configured to be inserted into the holes 15 in the flexible substrate 10. A first portion 320 is proximate the first side 302 of the fastener 300 and a second portion 340 is proximate a second side 304 of the fastener 300. The first portion 320 is symmetrical about the central plane 301 with the second portion 340. When inserted through the holes 15 in the flexible substrate 10, the first portion 320 and the second portion 340 positively retain the fastener 300 to the flexible substrate 10. For convenience, one side of the fastener 300 will be described in detail, where the second side is symmetrical about the plane 301 extending through the fastener 300 with respect to the first side described below.

When viewed from the side 302, the fastener 300 is generally "c-shaped." The fastener 300 includes an upper segment 307, which is configured to be positioned on one surface of the flexible substrate 10, and a lower segment 311, which is configured to be positioned on the opposite surface of the flexible substrate 10 when the fastener 300 is inserted into the flexible substrate. The upper segment 307 extends generally parallel to the lower segment 311 and is connected by a rear segment 309 extending between the upper and lower segments. A channel 313 is defined between the upper segment 307, rear segment 309, and lower segment 311, where the channel 313 has a width generally equal to or less than the thickness of the flexible substrate 10. The flexible substrate 10, therefore, fits within the channel 313 or is slightly compressed as it is inserted into the channel 313 while the fastener 300 is inserted through the holes 15 of the substrate.

The lower segment 311 includes a resilient member 322 having a width, W, greater than a width of the hole 15 in the flexible substrate 10. According to the embodiment illustrated in FIG. 20, the resilient member 322 is elongated with a first side member 324 that is arcuate and a second side member 326 that includes a first, curved segment 327 and a second, straight segment 329. The first, arcuate side member 324 extends generally from the rear side 306 to the front side 308 of the fastener 300. The second side member 326 meets the first side member 324 at a point 325 proximate the front side 308 of the fastener. The second side member 326 extends rearward from the point 325 but protrudes outwards from the first side 302 of the fastener. The first, curved segment 327 arches rearward and outward for a short distance and the second, straight segment 329 then extends at an angle from the side. The point 325 at the front of the resilient member 322 serves as a living hinge such that the straight segment 329 may be compressed toward the first arcuate side member 324 and pivot about the point 325. The resilient member 322 further includes a seat 323, or a recess, in which the end 328 of the straight segment 329 of the second side member 326 is received. The seat 323 provides a positive stop against which the second side member 326 may be compressed.

In order to insert the fastener 300 into the holes 15 of the flexible substrate 10, the two side members 324, 326 are pressed together such that the width, W, of the resilient member 322 is less than the width of the hole 15 in the substrate 10. As indicated above, pressing the two side members 324, 326 together causes the second side member 326 to pivot at the point 325 on the front of the resilient member and the end 328 of the straight segment 329 to engage the seat 323. The front end of the resilient member 322 is then inserted through the hole 15 and to the bottom side of the flexible substrate 10. When the resilient member 322 has passed through the hole 15, the side members 324, 326 are released and the second side member 326 returns to its original position. As a result, the width, W, of the resilient member 322 again becomes greater than the width of the hole 15, preventing the fastener 300 from pulling back through the hole 15. With the flexible substrate 10 located in the channel 313 of the fastener 300 and the resilient member 322 retaining the fastener 300 in the substrate 10, the fastener 300 is securely mounted to the flexible substrate 10.

The fastener 300 further includes a middle segment 330 configured to secure the antenna loop 30 to the flexible substrate 10. The middle segment 330 includes a channel 332 extending from the rear side 306 to the front side 308 of the fastener 300. The channel 332 starts at a height generally equal to the lower surface of the upper segment 307 and extends upward for a height generally equal to an expected thickness of the antenna loop 30. Thus, the channel 332 is configured to receive the antenna loop 30 and to positively retain the antenna loop 30 against the flexible substrate 10 and in a particular alignment on the flexible substrate 10.

Figure 25:
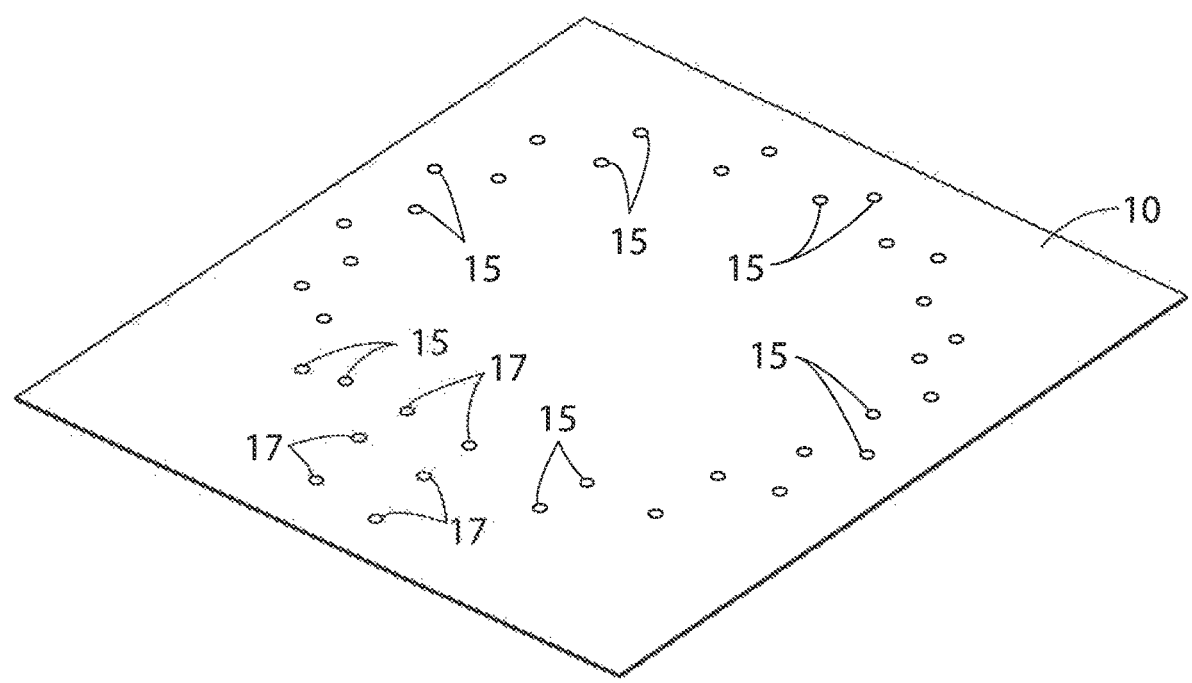
FIG. 25 is an isometric view of the flexible substrate of FIG. 24.
Figure 26:
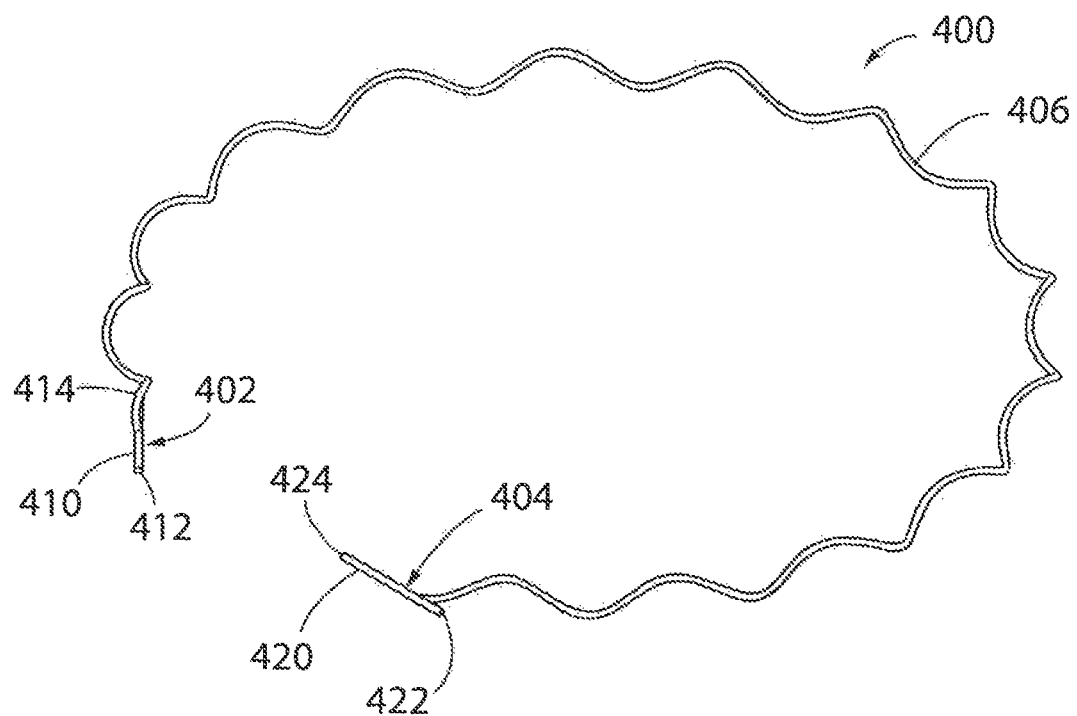
FIG. 26 is an isometric view of a fastener to secure the antenna loop to the flexible substrate according to the embodiment shown in FIG. 24.
Figure 27:
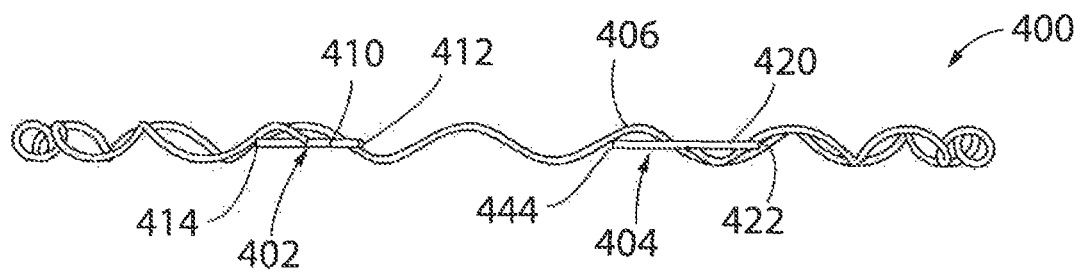
FIG. 27 is a front elevation view of the fastener of FIG. 26.
Figure 28:
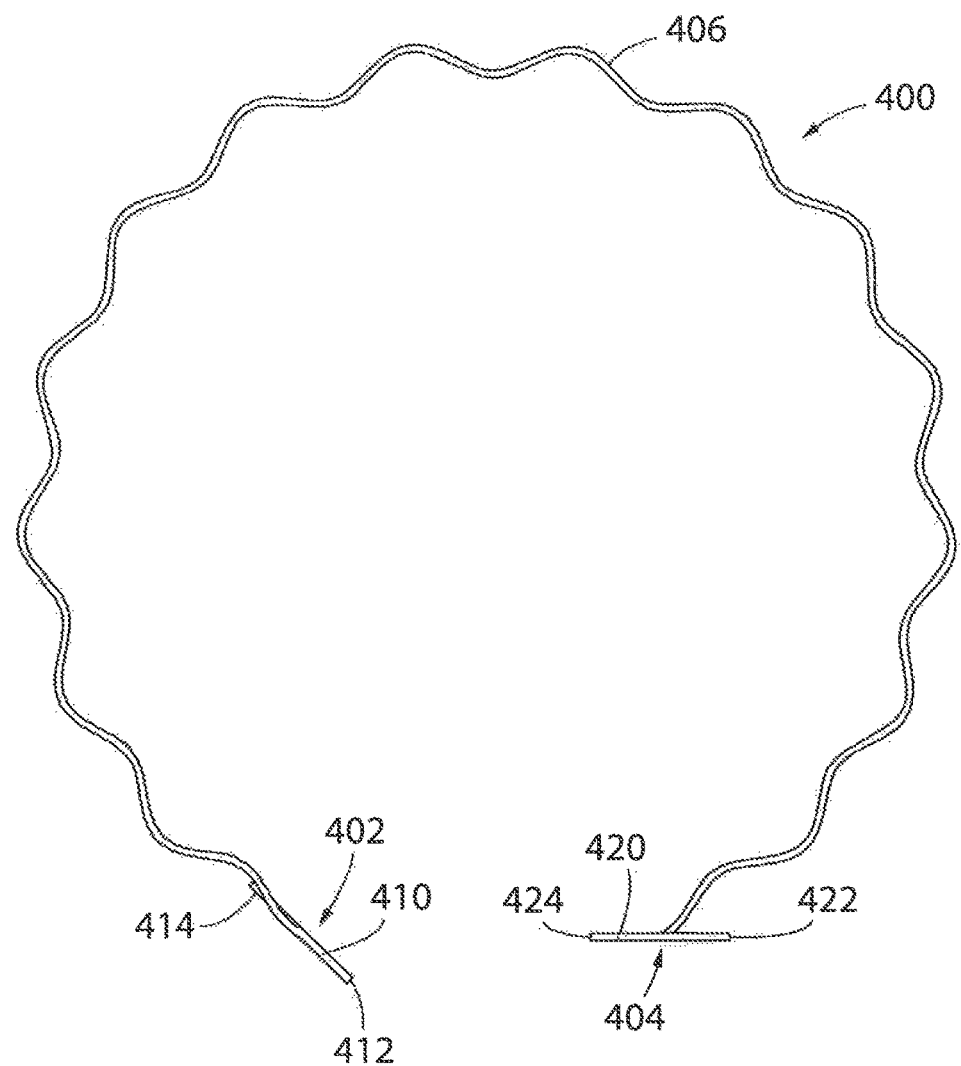
FIG. 28 is a top plan view of the fastener of FIG. 26.
Figure 29:
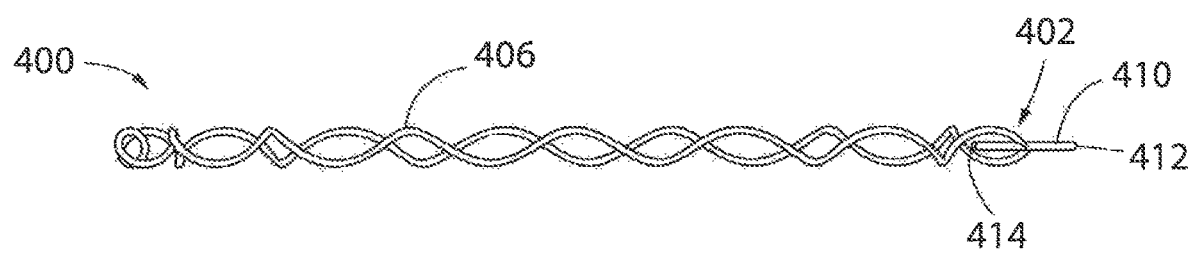
FIG. 29 is a side elevation view of the fastener of FIG. 26.

Turning next to FIGS. 24-29, a fourth embodiment of a fastener 400 to secure the antenna loop 30 to the flexible substrate 10 is illustrated. Similar to the other embodiments, the fastener 400 is configured to secure an antenna loop 30 to a flexible substrate 10. As shown in FIG. 25 a series of holes 15, 17 are made through the flexible substrate 10. The holes 15, 17 may be cut, for example, by drilling, stamping, die cutting, laser cutting, or the like in the flexible substrate 10. A first series of holes 15 are provided to receive the fastener 400 or a portion of the fastener extending through the hole 15. A second series of holes 17 are provided for securing a circuit board or housing 20 containing a circuit board on which an electronic circuit for the antenna loop 30 is mounted. The illustrated embodiment shows the housing 20 as a rectangular box. It is contemplated that various other shapes for the housing 20 may be utilized. Optionally, the circuit board may also be mounted directly to the flexible substrate 10. Unlike the other embodiments, the fastener 400 is a single continuous member that extends through each of the holes 15 for the fastener 400 rather than providing multiple fasteners at intervals spaced apart along the length of the antenna loop 30.

Referring to FIGS. 26-29, the fastener 400 is a single, elongated member configured to be fed through each of the holes 15 and to secure one of the antenna loops 30 to the substrate 10. The fastener 400 may have, for example, an extruded body 406 having a cylindrical sectional area. Optionally, the fastener 400 may have other sectional areas without deviating from the scope of the invention. The fastener 400 is preferably constructed of a flexible plastic material and may further be formed in a helical, or other spiral, configuration along the length of the fastener 400. The helical configuration is molded such that the spiral assists in feeding the fastener 400 through each of the holes 15 and around the antenna loop 30 located on the substrate 10. The fastener 400 may further be formed in a ring-shape, having a diameter corresponding to a diameter of the antenna loop 30. The material from which the fastener 400 is made is preferably a resilient material, such that the body 406 of the fastener 400 will maintain the helical form along its length and the ring-shape absent a force applied to the fastener 400. The fastener 400 may deflect axially or radially along the length of the body 406 as it is being inserted into the substrate 10 and return to its original shape when an external force is no longer applied.

The body 406 of the fastener 400 extends from a first end 402 to a second end 404, where each end 402, 404 of the fastener is located proximate one side of the housing 20 for the signal conditioning circuit when the fastener is securing an antenna loop 30 to the substrate 10. A first tab 410 is connected to the first end 402 of the fastener 400, and a second tab 420 is connected to the second end 404 of the fastener 400. Each tab 410, 420 may be integrally formed with the body 406 of the fastener 400, for example, through a molding process. Optionally, each tab may be joined to the body via any suitable method, such as applying solvents or adhesives, or using thermal, induction, or vibrational welding of the members. Each tab 410, 420 has preferably the same sectional area of the body 406 and a middle portion of the tab 410, 420 is joined to the respective end 402, 404 of the body 406. The first tab 410 includes a first end 412 and a second end 414, and the second tab 420 similarly includes a first end 422 and a second end 424. When each tab 410, 420 is joined to the body 406 it is generally perpendicular to the end of the body. The point at which each tab 410, 420 is joined to the body 406 forms a living hinge, such the tab may be pivoted about the connection such that one end of the tab 410, 420 may be aligned adjacent to the body 406 and the other end of the tab 410, 420 protrudes in an axial direction from the end of the body 406. The tab is pivoted back such that it is adjacent the body 406 of the fastener 400 as the fastener 400 is inserted through the holes 15 or to remove the fastener 400 from one of the holes 15. After inserting the fastener 400 through a hole 15 and, in particular, after inserting the fastener through the last hole, the tab is allowed to return to its original position, which is generally perpendicular to the body 406 of the fastener. In its original position, the tab 410, 420 prevents the fastener from being pulled through the hole 15.

Turning next to FIGS. 32-41 a fifth embodiment of a fastener 500 to secure the antenna loop 30 to the flexible substrate 10 is illustrated. The fastener is of single-part, molded construction. The fastener 500 includes a base 510 and two members extending from the base 510. A first member 520 is longer than the second member 540, and both members 520, 540 are configured to be inserted through one of the holes 15 in the flexible substrate 10. Optionally, the distal end of each protruding member with respect to the base may have a piercing member to engage the flexible substrate 10 at a piercing point and create a hole 15 in the flexible substrate 10 as the fastener is inserted.

Figure 44:
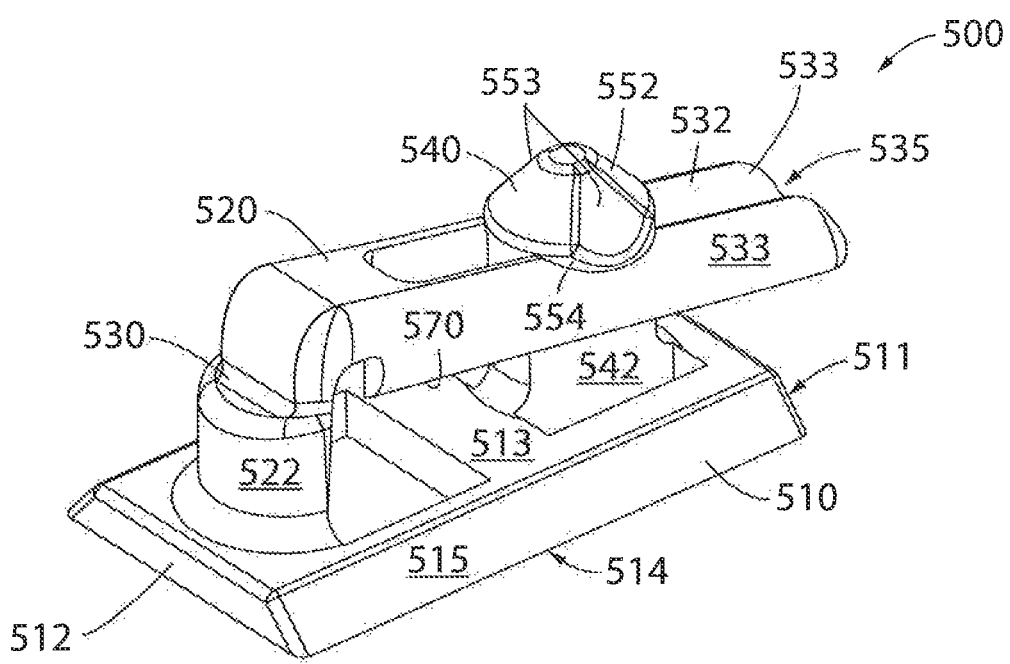
FIG. 44 is an isometric view of the fastener of FIG. 42 in a closed position.
Figure 45:
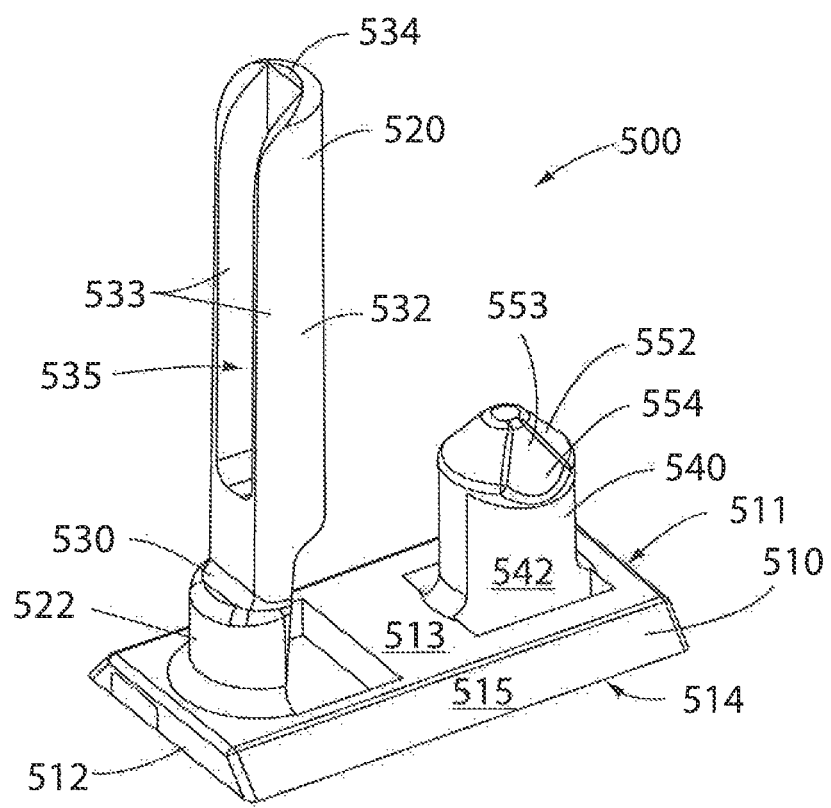
FIG. 45 is an isometric view of the fastener of FIG. 42 in an open position.

According to the illustrated embodiment of the fastener 500, the base 510 is a generally rectangular member. The base 510 includes a front surface 511, a rear surface 512 opposite the front surface, a top surface 513, a bottom surface 514 opposite the top surface, and two side surfaces 515, where the front surface 511, rear surface 512, and the side surfaces 515 extend between the top and bottom surfaces. Although illustrated as a generally rectangular member, it is contemplated that the base 510 may be of any shape that extends between the first member 520 and the second member 540 to establish a spatial relationship between the two members such that each of the two members may be inserted through separate holes 15 in the flexible substrate together. Further, the top surface 513 may be joined to the side surfaces 515, the front surface 511, and the rear surface 512 at a square edge, curved edge, or tapered edge. Similarly, each of the side, front, and rear surfaces (515, 511, and 512, respectively) may be oriented perpendicular to the top surface 513 or curved or sloped with respect to the top surface 513 (FIGS. 44-45).

The first member 520 includes a first segment 522 and a second segment 532, where the two segments 522, 532 are joined by a living hinge 530. The first segment 522 extends for a first height which is greater than the thickness of the flexible substrate 10 and an antenna loop 30. Thus, when the first member 520 is inserted through the flexible substrate 10, the flexible substrate generally resides around the first segment 522 of the first member 520. The living hinge 530 extends for a width of the first member 520 between the first segment 522 and the second segment 532. The living hinge 530 is formed of the same material as the first and second segments, but is of a reduced thickness, such that the second segment 532 of the first member 520 is pivotally moved about the living hinge 530 and may be rotated forward and in a downward direction toward the second member 540 of the fastener 500 to close the fastener. The second segment 532 of the first member 520 includes two side pieces 533 each extending from the living hinge 530 to an end piece 534. An opening 535 is defined through the second segment 532 of the first member 520 by the living hinge 530, the two side pieces 533, and the end piece 534. The opening 535 is configured to receive the second segment 552 of the second member 540.

The second member 540 also includes a first segment 542 and a second segment 552 where the two segments are rigidly coupled. The first segment 542 extends from the base for a first height which is greater than the thickness of the flexible substrate 10. Thus, when the second member 540 is inserted through the flexible substrate 10, the flexible substrate generally resides around the first segment 542 of the second member. The second segment 552 of the second member 540 is configured to receive the second segment 532 of the first member 520. The upper end of the second segment 552 includes at least one tapered surface 553. As shown, for example, in FIGS. 34-37, the tapered surface 553 forms a partial conical surface extending around the entire periphery of the second segment 552. According to another embodiment, the tapered surface 553 is located along either side of the second segment 552. As shown, for example, in FIGS. 44-45, a first tapered surface may extend to the front and rear of the second segment 552 and a second tapered surface 553 may extend to either side of the second segment 552. The width of the second segment 552 of the second member 540 is greater than the width of the first segment 542 of the second member 540 such that tabs 554 are formed that protrude outward from a central axis of the second member 540 at the junction between the second segment 552 and the first segment 542 of the second member 540.

The tabs 554 on the second segment 552 of the second member 540 are configured to positively retain the second segment 532 of the first member 520 to the second segment 552 of the second member 540. The tapered surface 553 to the sides of the second segment 552 of the second member 540 are configured to engage the inner periphery of the opening 535 of the second segment 532 of the first member 520. The width of the second segment 552 of the second member 540 at the tabs 554 is greater than the width of the opening 535. Thus, as the second segment 532 of the first member 520 slides down along the tapered surface 553, the side pieces 533 are deflected outward allowing the second segment 552 of the second member 540 to fit between the side pieces 533 and through the opening 535. When the second segment 532 of the first member 520 has rotated downward past the tabs 554 of the second member 540, the side pieces 533 of the first member 520 return to their original width and are captured below the tabs 554 of the second member 540. To release the second segment 532 of the first member 520, a tool may be inserted in the opening 535 to spread the side pieces 533, allowing the second segment 532 of the first member 520 to be rotated upward past the tabs 554 of the second member 540.

When the second segment 532 of the first member 520 is secured to the second segment 552 of the second member 540 by the tabs 554, a channel 570 is defined in the fastener 500 that is configured to secure an antenna loop 30 to the flexible substrate 10. The channel 570 is defined by the top surface 513 of the base 510, the two sides of the first and second members facing each other, and the lower surface of the second segment 532 of the first member 520 when it is retained by the tabs 554 of the second member 540.

Figure 30:
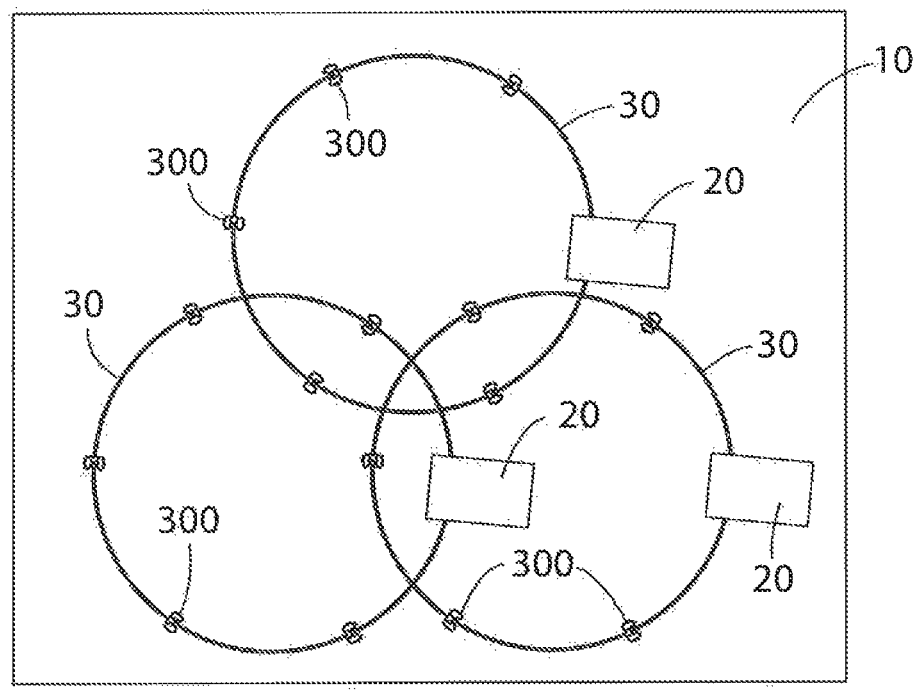
FIG. 30 is a top plan view of multiple antenna loops secured to the flexible substrate using the fastener of FIG. 17.
Figure 31:
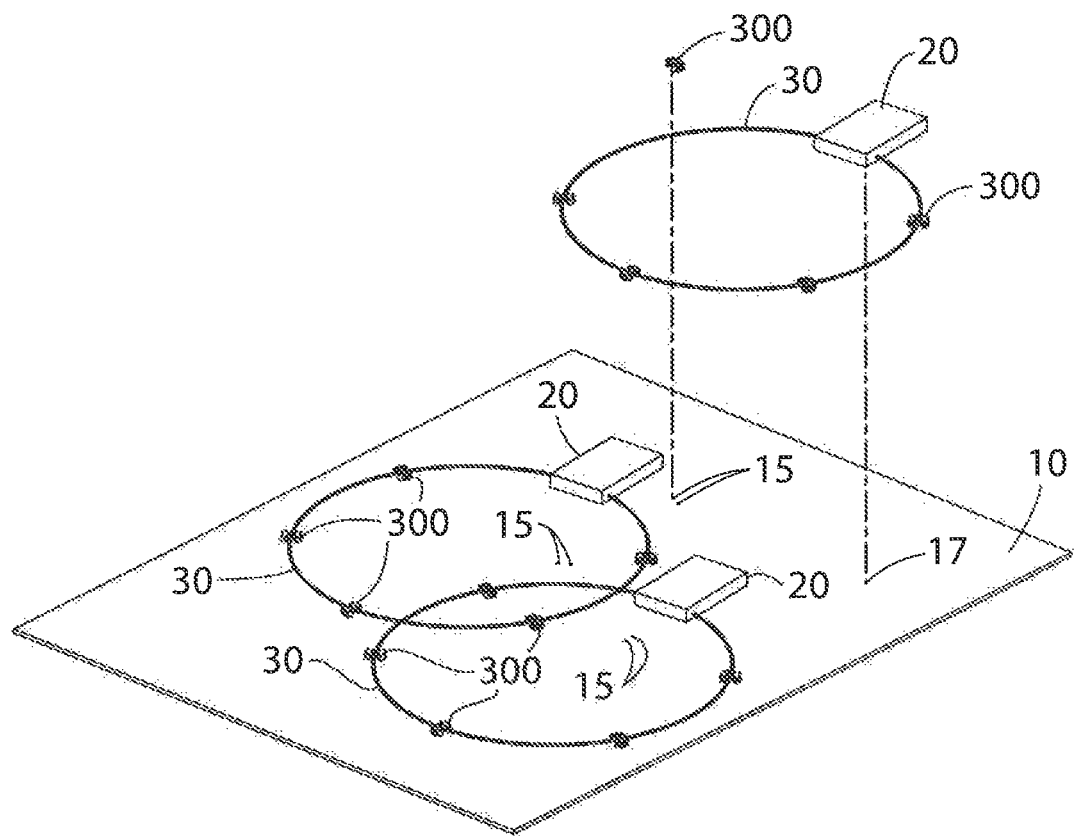
FIG. 31 is an isometric, partial exploded view of the antenna array of FIG. 30.

In operation, one embodiment of the fasteners 100, 200, 300, 400, 500 described above is used to secure one or more antenna loops 30 to a flexible substrate 10 to form a flexible antenna array. Referring to FIGS. 30 and 31, the fastener 300 of FIGS. 17-23 is illustrated securing multiple antenna loops 30 to a flexible substrate 10. Each fastener 300 is inserted through a pair of holes 15 such that the channel 332 secures the antenna loop 30 to the flexible substrate 10. The fasteners 300 are configured to engage the flexible substrate 10 to prevent movement of the fastener 300 with respect to the flexible substrate. For example, the rear segment 309 of the fastener 300 is sized complementary to the size of the hole 15 such that the fastener does not move within the hole 15. Similarly, the width of the channel 313 is complementary to the width of the flexible substrate 10 to engage both sides of the flexible substrate and to further prevent movement of the fastener with respect to the substrate. The holes 15 are cut in the substrate 10 to position the fastener 400 or fasteners 100, 200, 300, 500 and when multiple antenna loops 30 are mounted to the flexible substrate 10, the fastener 400 or fasteners 100, 200, 300, 500 maintain the desired alignment of the antenna loops 30 with respect to each other as the flexible substrate 10 is positioned on the object to be imaged.

Figure 32:
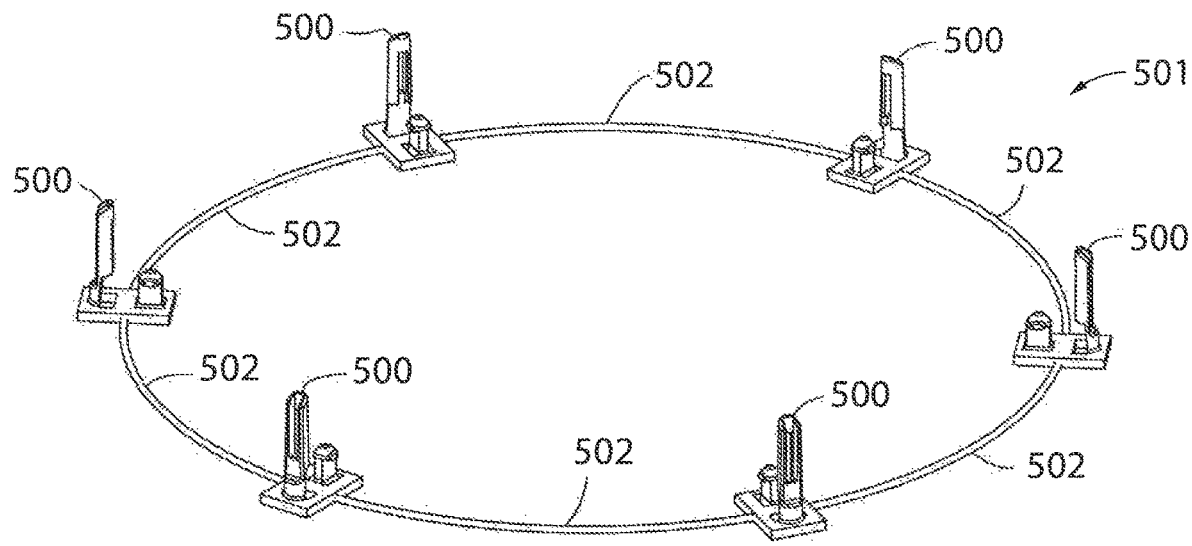
FIG. 32 is an isometric view of a set of fasteners to secure the antenna loop to the flexible substrate with one embodiment of a connecting member according to another embodiment of the present invention.
Figure 33:
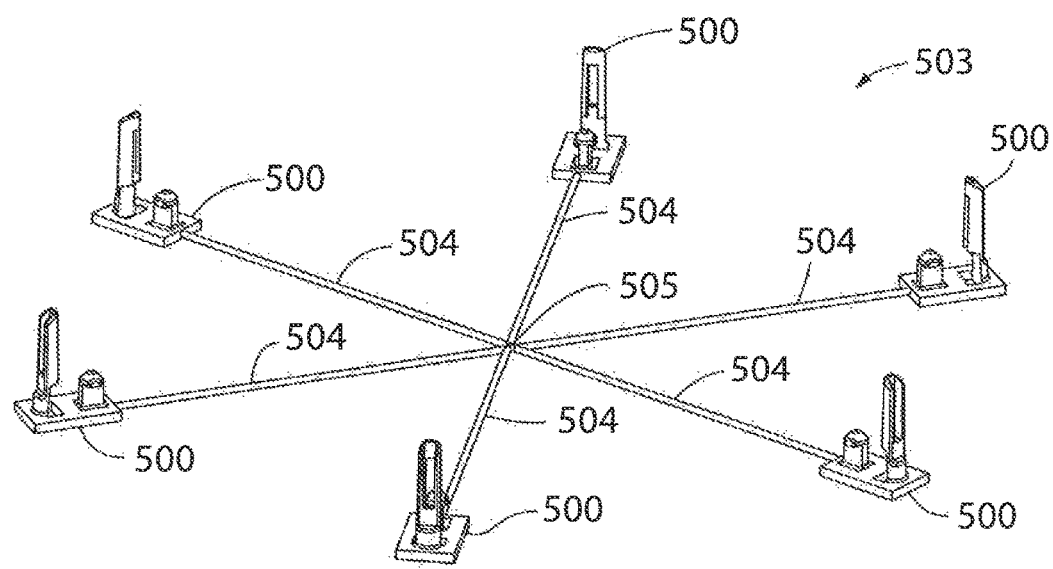
FIG. 33 is an isometric view of a set of fasteners to secure the antenna loop to the flexible substrate with another embodiment of a connecting member according to another embodiment of the present invention.
Figure 34:
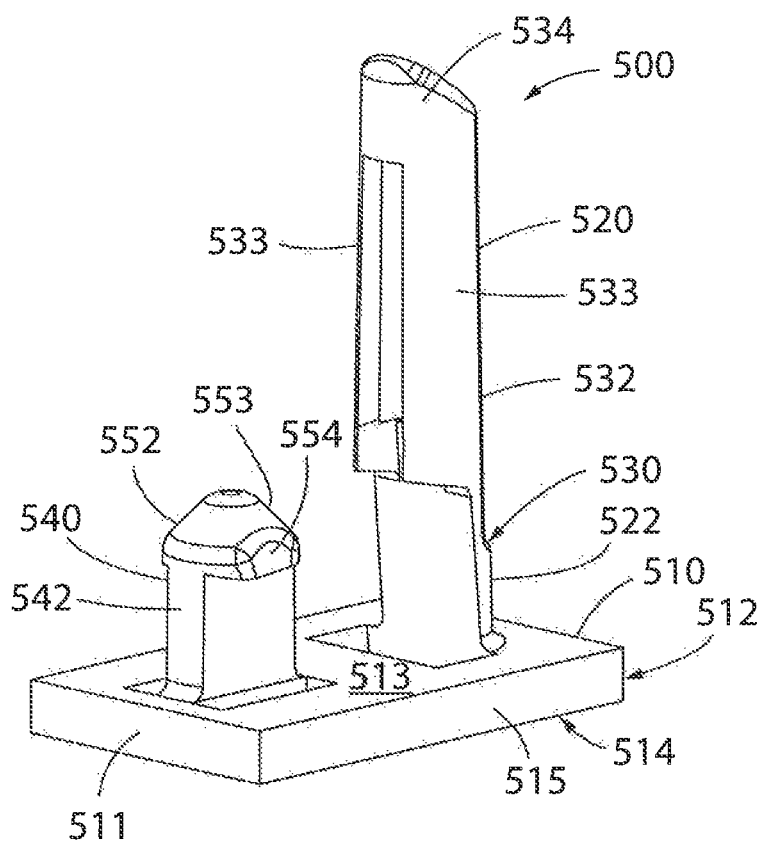
FIG. 34 is an isometric view of the fastener of FIG. 32 in an open position.
Figure 35:
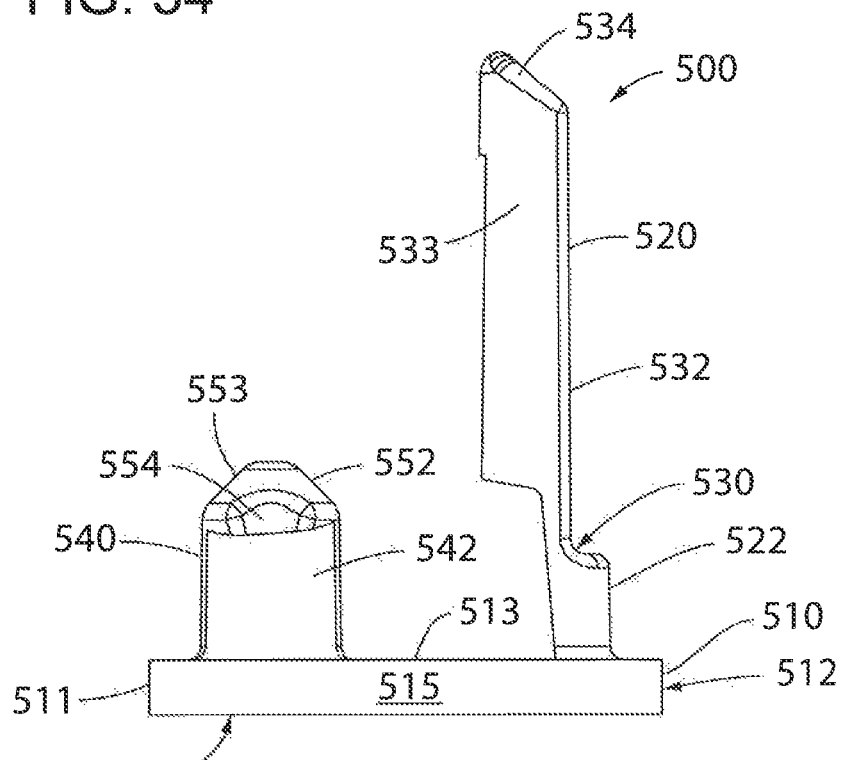
FIG. 35 is a side elevation view of the fastener of FIG. 32 in an open position.
Figure 36:
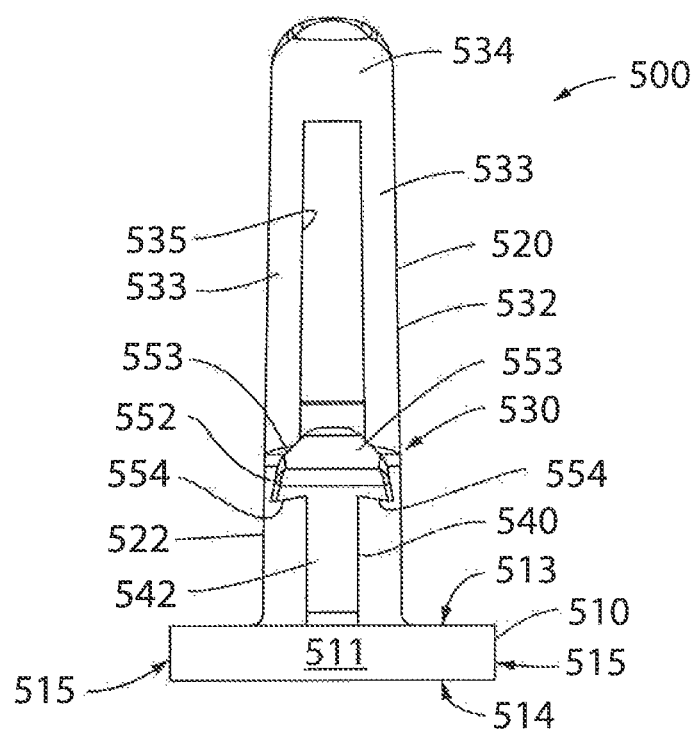
FIG. 36 is a front elevation view of the fastener of FIG. 32 in an open position.
Figure 37:
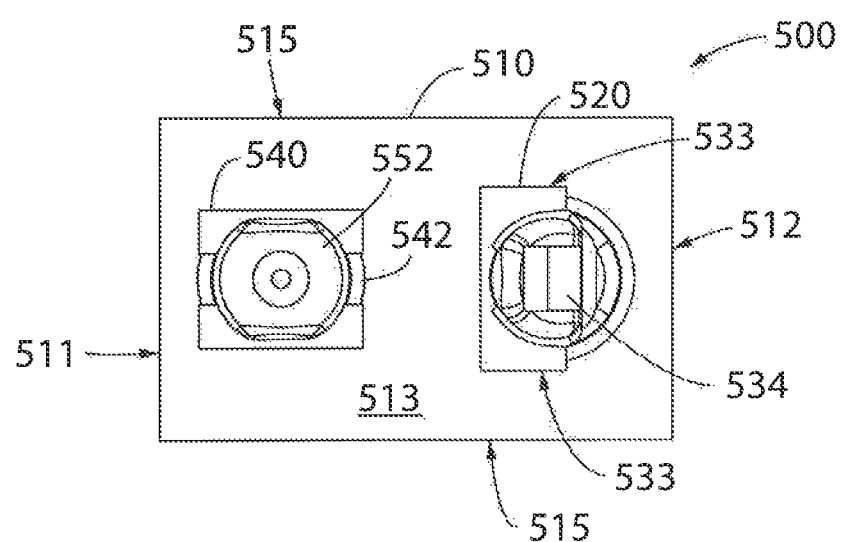
FIG. 37 is a top plan view of the fastener of FIG. 32 in an open position.
Figure 38:
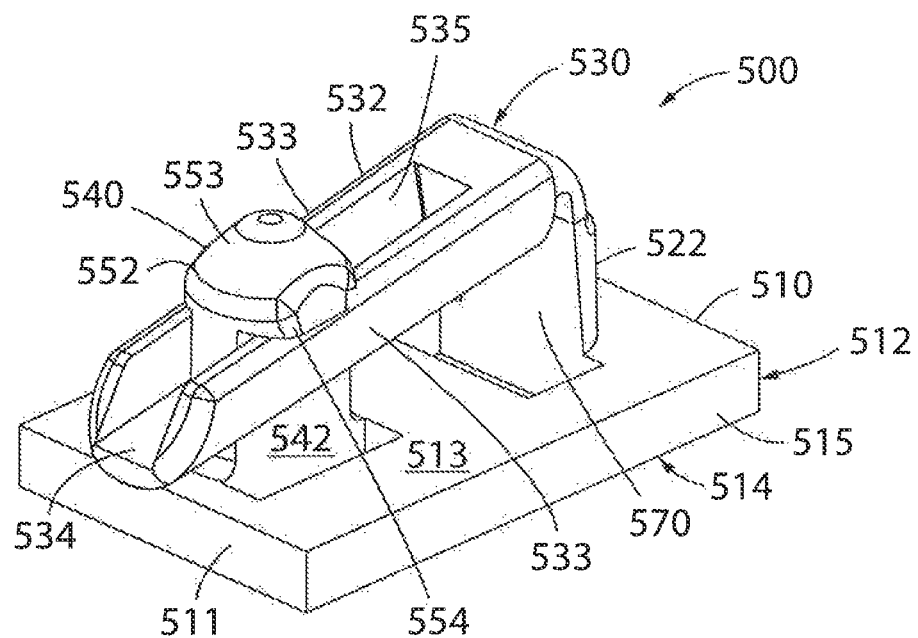
FIG. 38 is an isometric view of the fastener of FIG. 32 in a closed position.
Figure 39:
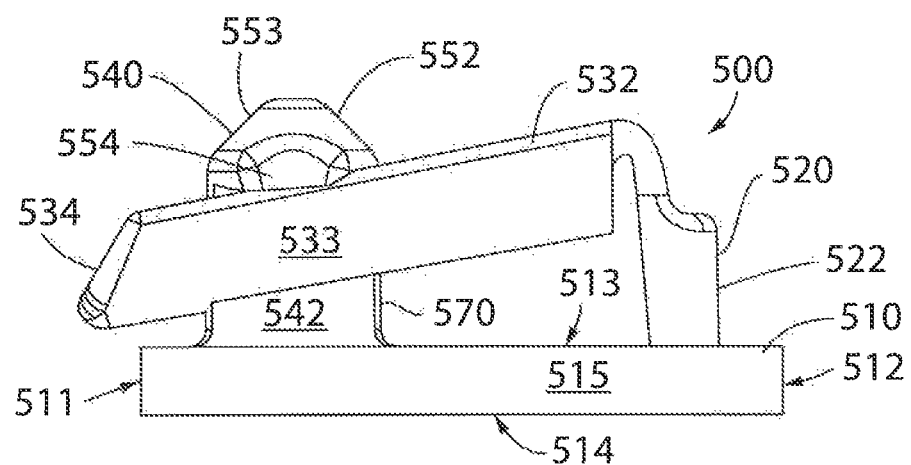
FIG. 39 is a side elevation view of the fastener of FIG. 32 in a closed position.
Figure 40:
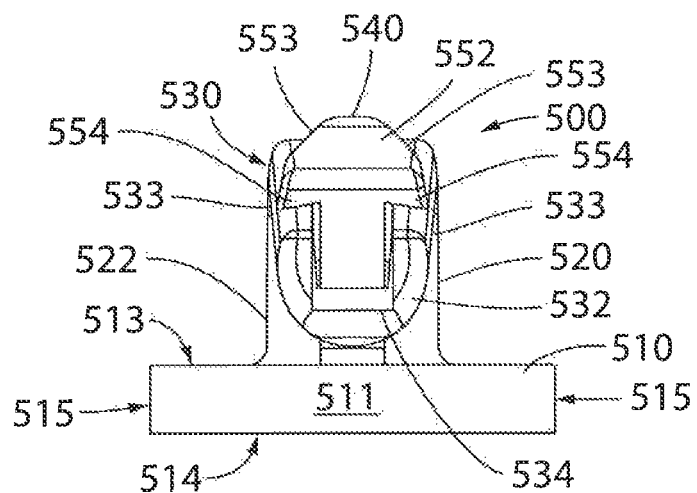
FIG. 40 is a front elevation view of the fastener of FIG. 32 in a closed position.
Figure 41:
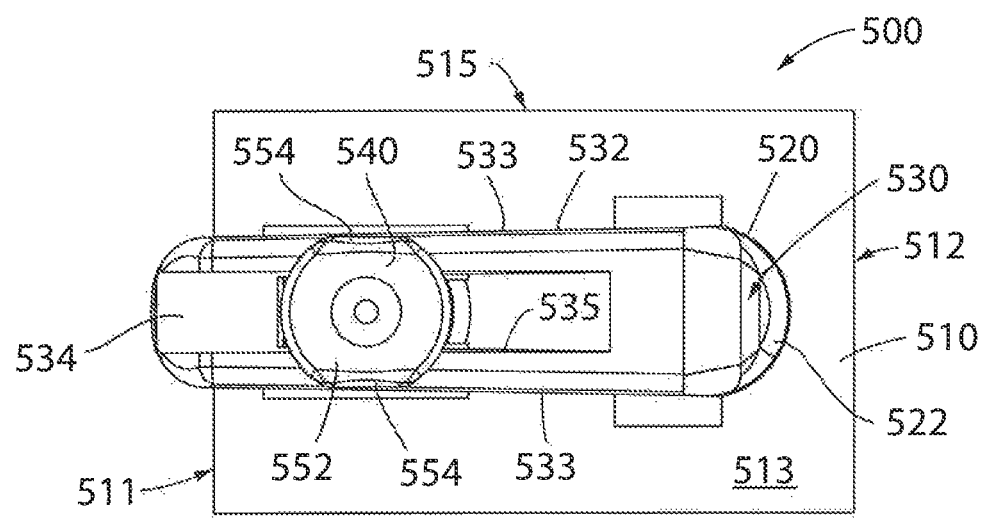
FIG. 41 is a top plan view of the fastener of FIG. 32 in a closed position.
Figure 42:
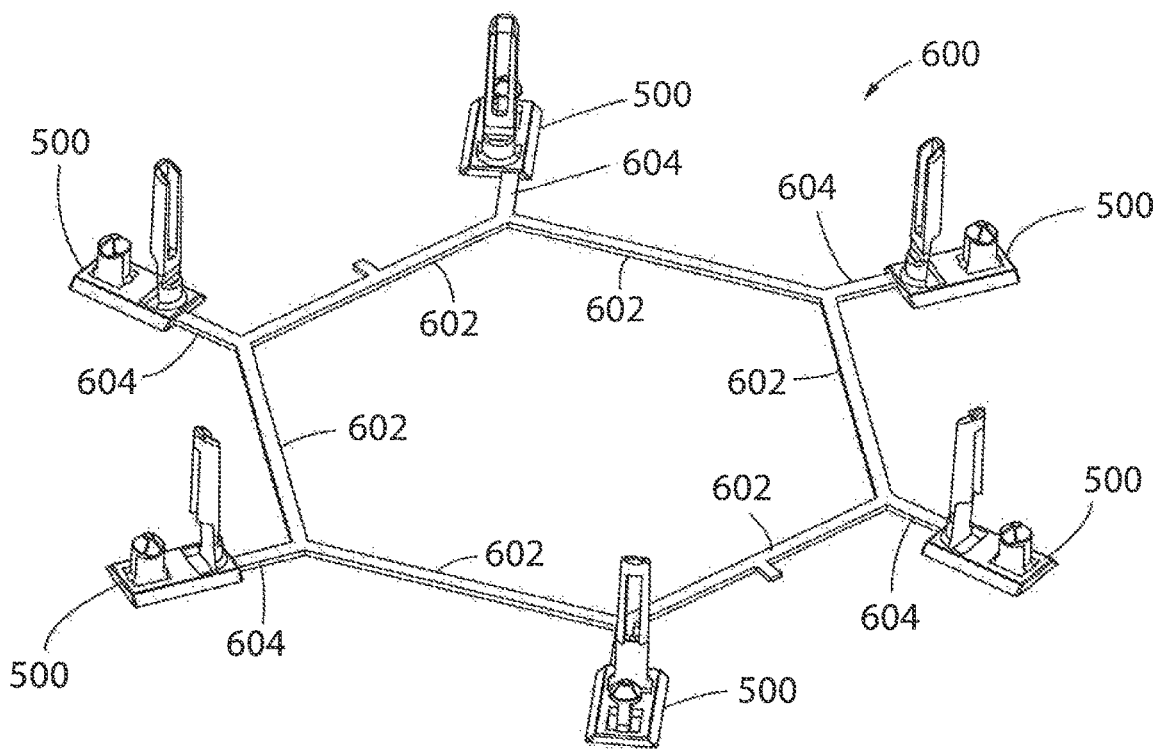
FIG. 42 is an isometric view of a set of fasteners to secure the antenna loop to the flexible substrate in an open position with another embodiment of a connecting member according to another embodiment of the present invention.

According to another aspect of the invention, the fasteners 500 may be mounted to a web to form a fastener assembly 501, 503, 600 (see e.g., FIGS. 32, 33, and 42). The fastener assemblies 501, 503, 600 include multiple fasteners 500 used to secure a single antenna loop 30, where the web includes a number of interconnect segments used to align the fasteners 500 with the holes 15 in the flexible substrate 10.

With reference to FIG. 32, a first embodiment of a fastener assembly 501 is illustrated. The fastener assembly 501 includes a web formed from a number or arcuate segments 502. Each arcuate segment 502 has a first end and a second end, where each of the first and second ends are joined to a side surface 515 of the base 510 of one of the fasteners 500. Each arcuate segment 502 may have a radius equal to the radius of the antenna loop 30 and is joined between side surfaces 515 of two adjacent fasteners 500. The arcuate segments 502 align each fastener 500 with a set of holes 15 through which the first and second members 520, 540 of each fastener 500 may be inserted. After the fasteners 500 are inserted through the holes 15 in the flexible substrate 10 and closed to secure the antenna loop 30, the arcuate segments 502 may be cut away and removed such that the arcuate segments 502 do not limit the flexibility of the flexible substrate 10 to which the fasteners 500 are mounted.

With reference to FIG. 33, a second embodiment of a fastener assembly 503 is illustrated. The fastener assembly 503 includes a web formed from a number of straight segments 504. Each straight segment 504 has a first end and a second end, where the first end of each straight segment 504 is connected at a central point 505 and the second end of each straight segment 504 is joined to a front surface 511 of the base 510 of one of the fasteners 500. The straight segments 504 are connected in a star configuration and, similar to the arcuate segments 502 discussed above, align the fasteners 500 with a set of holes 15 through which the first and second members 520, 540 of each fastener 500 may be inserted. After the fasteners 500 are inserted through the holes 15 in the flexible substrate 10 and closed to secure the antenna loop 30, the straight segments 504 may be cut away and removed such that the straight segments 504 do not limit the flexibility of the flexible substrate 10 to which the fasteners 500 are mounted.

Figure 43:
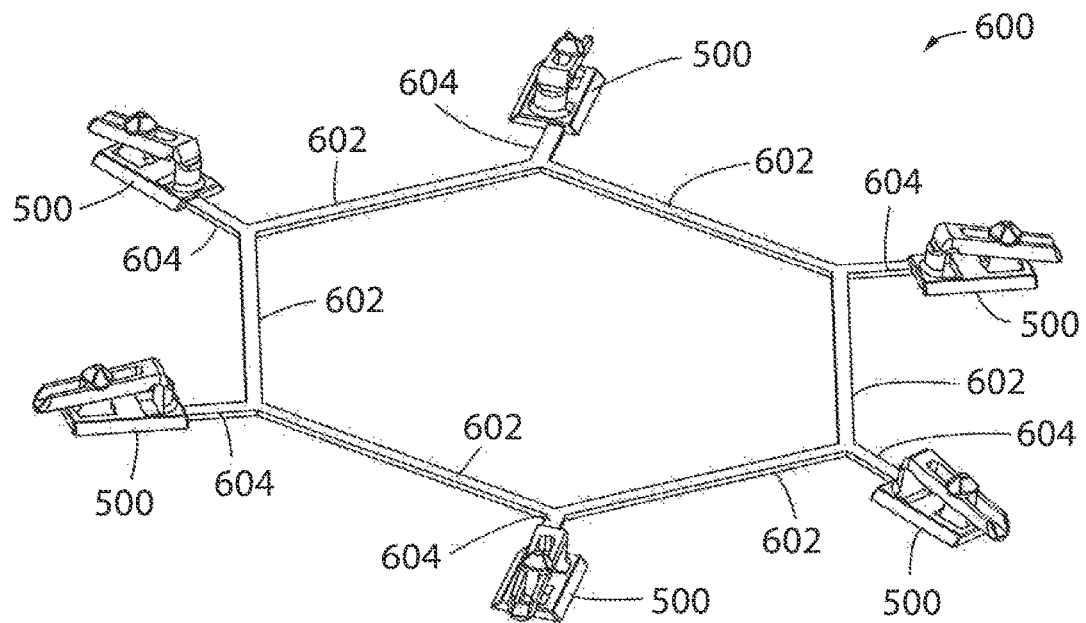
FIG. 43 is an isometric view of the set of fasteners and connecting member of FIG. 42 with the fasteners in a closed position.

With reference next to FIGS. 42, 43, still another embodiment of a fastener assembly 600 is illustrated. The fastener assembly 600 includes a web formed from two sets of straight segments. A first set of straight segments 602 is joined in an end-to-end manner, where a first end of one segment from the first set of straight segments 602 is joined to a second end of another segment from the first set of straight segments 602. The first set of straight segments 602 may be formed as a single member or formed by joining separate members via any suitable method, such as vibration, heat, or ultrasonic welding. A second set of straight segments 604 is connected between the first set of straight segments 602 and each fastener 500. A first end of each segment in the second set of straight segments 604 is connected to one of the first segments or, optionally, connected at a junction between two of the first segments, and a second end of each segment in the second set of straight segments 604 is connected to one of the fasteners 500. It is contemplated that the first and second set of straight segments 602, 604 may be integrally formed as a single member, for example, via injection molding. Similarly, the fasteners 500 may also be integrally formed with the web to create the fastener assembly 600. Optionally, the fasteners 500, the first set of straight segments 602, and the second set of straight segments 604 may be formed of various different separate members and joined via any suitable method, such as vibration, heat, or ultrasonic welding.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A system for assembling a flexible antenna array for medical imaging, the system comprising:
   a flexible substrate including a plurality of holes extending therethrough;
   a plurality of antennas operative to receive a signal corresponding to an anatomical region of a patient during medical imaging; and
   a plurality of fasteners, wherein each fastener is removably mounted to the flexible substrate, each fastener extends through at least one of the plurality of holes in the flexible substrate, and each fastener is operative to secure one of the plurality of antennas to the flexible substrate.

2. The system of claim 1 wherein each fastener extends through a first hole and a second hole in the flexible substrate and wherein each antenna is positioned between the first hole and the second hole for one of the plurality of fasteners when secured to the flexible substrate.

3. The system of claim 2 wherein each of the plurality of fasteners includes:
   a first member having a first segment, configured to extend through the first hole in the flexible substrate, and a second segment, pivotally mounted to the first segment;
   a second member configured to extend through the second hole in the flexible substrate, wherein the second segment of the first member pivots towards and positively engages the second member to retain one of the plurality of antennas to the flexible substrate.

4. The system of claim 3 wherein the first member further includes a living hinge between the first segment and the second segment.

5. The system of claim 2 further comprising a web connected to each of the plurality of fasteners operative to secure a first antenna to the flexible substrate, wherein the web is operative to position each of the fasteners proximate to the first hole and the second hole in the flexible substrate through which the fastener extends.

6. The system of claim 5 wherein:
   the web includes a plurality of segments,
   each of the plurality of segments includes a first end and a second end, the first end of each of the plurality of segments is connected to a first fastener, selected from the plurality of fasteners, and the second end of each of the plurality of segments is connected to a second fastener, selected from the plurality of fasteners.

7. The system of claim 5 wherein:
the web includes a plurality of segments,
each of the plurality of segments includes a first end and a second end,
the first end of each of the plurality of segments is connected together at a central point, and
the second end of each of the plurality of segments is connected to one of the plurality of fasteners.

8. The system of claim 5 wherein:
the web includes a plurality of first segments and a plurality of second segments,
each of the plurality of first segments includes a first end and a second end,
the first end of each first segment is connected to the second end of another first segment,
each of the plurality of second segments includes a first end and a second end,
the first end of each of the plurality of second segments is connected to one of the first segments, and
the second end of each of the plurality of second segments is connected to one of the plurality of fasteners.

9. A system for assembling a flexible antenna array for medical imaging, the system comprising:
a flexible substrate including a plurality of holes extending therethrough;
a plurality of antennas operative to receive a signal corresponding to an anatomical region of a patient during medical imaging; and
a plurality of fasteners, wherein each fastener includes:
a base,
a first member having a first segment and a second segment pivotally mounted to the first segment, wherein the first member extends from the base, and
a second member extending from the base in the same direction as the first member, wherein each of the first and second members are configured to extend through one of the plurality of holes in the flexible substrate and the second segment of the first member pivots towards and is removably connected to the second member to retain one of the plurality of antennas to the flexible substrate.

10. The system of claim 9 wherein the first member further includes a living hinge between the first segment and the second segment, wherein the second segment is pivotally mounted to the first segment via the living hinge.

11. The system of claim 9 wherein,
the first member of each fastener includes a first piercing member, the second member of each fastener includes a second piercing member, and
the plurality of holes in the flexible substrate are cut by the first and second piercing members when each of the plurality of fasteners is inserted through the flexible substrate.

12. The system of claim 9 further comprising a web connected to each of the plurality of fasteners operative to secure a first antenna to the flexible substrate, wherein the web is operative to position each of the first and second members proximate to the corresponding hole in the flexible substrate through which the first and second members extend.

13. A method for assembling a flexible antenna array for medical imaging, the method comprising the steps of:
creating a plurality of holes through a flexible substrate;
positioning a plurality of antennas on the flexible substrate, wherein each of the plurality of antennas is operative to receive a signal corresponding to an anatomical region of a patient during medical imaging;
inserting a plurality of fasteners through the flexible substrate, wherein each of the plurality of fasteners includes:
a first member having:
a first segment, configured to extend through a first hole in the flexible substrate, the first hole selected from the plurality of holes, and
a second segment, pivotally mounted to the first segment; and
a second member configured to extend through a second hole in the flexible substrate, the second hole selected from the plurality of holes; and
pivoting the second segment of the first member for each of the plurality of fasteners towards the second member such that the second segment of the first member positively engages the second member to retain one of the plurality of antennas to the flexible substrate.

14. The method of claim 13 wherein:
the first member of each fastener includes a first piercing member,
the second member of each fastener includes a second piercing member, and
the step of creating the plurality of holes through the flexible substrate is performed by the first and second piercing members during the step of inserting the plurality of fasteners through the flexible substrate.

15. The method of claim 13 further comprising the step of positioning the plurality of fasteners used to secure one of the plurality of antennas in tandem by a web connected between the plurality of fasteners for the corresponding antenna.

* * * * *